(12) United States Patent
Harland

(10) Patent No.: US 6,780,611 B1
(45) Date of Patent: Aug. 24, 2004

(54) POLYNUCLEOTIDE ENCODING NEUROMEDIN U RECEPTOR

(75) Inventor: Lee Harland, Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/684,725

(22) Filed: Oct. 6, 2000

(30) Foreign Application Priority Data

Oct. 8, 1999 (GB) ............................................. 9923888

(51) Int. Cl.[7] ........................ C12N 15/00; C12N 15/63; C12N 15/85; C12N 1/21; C07H 21/04
(52) U.S. Cl. .................. 435/69.1; 435/320.1; 435/325; 435/252.3; 435/254.11; 536/23.5
(58) Field of Search .............................. 536/23.5, 23.1, 536/24.3; 435/320.1, 325, 252.3, 254.11, 254.2, 69.1, 254.1, 455

(56) References Cited

FOREIGN PATENT DOCUMENTS

| WO | WO9955732 | 11/1999 |
|---|---|---|
| WO | WO0022131 | 4/2000 |

OTHER PUBLICATIONS

Database EMBL Accession No. AC008571, May 5, 2000.*
Peer Bork and Eugene V. Koonin, Predicting functions from protein sequences—where are the bottlenecks? Nature Genetics 18:313–318, 1998.*
Ji et al. G–protein–coupled receptors, J. Biol. Chem., 273:17299–17302, 1998.*
Hosoya, M., et al., Journal of Biological Chemistry, 275 (38): 29528–29532, 2000.
Howard, A., et al., Nature, 406 (6791): 70–74, 2000.
Shan, L., et al., Journal of Biological Chemistry, 275 (50): 39482–39486, 2000.
Database EMBL Accession No. AC008571 (1999).
Tan, C., et al., Genomics, 52: 223–229, 1998.
Behr et al., QJ Nucl Med v 43 pp 268–280 (1999).
Eckard et al., Curr Med Chem v7 pp897–910 (2000).
"PROBFIND: A Computer Program for Searching Probes for Peptide Sequences," NAR 14, 567–570 (1986).
Howard, A., et al., Letters to Nature, Identification of receptors for neuromedin U and its role in feeding, vol. 406, 70–74, 2000.
Nandha, K., et al., Endocrinology, 'Characterization of the rat uterine neuromedin u receptor,' vol. 133(2): 482–486, 1993.

* cited by examiner

Primary Examiner—Gary Kunz
Assistant Examiner—Ruixiang Li
(74) Attorney, Agent, or Firm—Peter C. Richardson; Gregg C. Benson; Deborah A. Martin

(57) ABSTRACT

Polynucleotide and polypeptide sequences are described. The polypeptide sequences comprise one or more of: (a) a polypeptide having the deduced amino acid sequence translated from the polynucleotide sequence in SEQ ID NO: 1 and variants, fragments, homologues, analogues and derivatives thereof; (b) a polypeptide of SEQ ID NO: 2 and variants, fragments, homologues, analogues and derivatives thereof; or (c) a polypeptide encoded by the cDNA of NCIMB 41066 and variants, fragments, homologues, analogues and derivatives thereof.

8 Claims, 6 Drawing Sheets

Figure 3

```
CLUSTAL W (1.74) multiple sequence alignment

NTR1_RAT        MHLNSSVPQGTPGEPDAQPFSGPQSEMEATFLALSLSNGSGNTSESDTAGPNSDLDVNTD
PFI-002         ------------MEKLQNASWIYQQKLEDPFQKH------LNSTEEYLAFLCGPRRS---
                            *  :.    *.::* .*        *::*. *   .

NTR1_RAT        IYSKVLVTAIYLALFVVGTVGNSVTAFTLARKKSLQSLQSTVHYHLGSLALSDLLILLLA
PFI-002         HF-FLPVSVVYVPIFVVGVIGNVLVCLVILQ---HQAMKTPTNYYLFSLAVSDLLVLLLG
                 :  : *:.:*:.:****..:** :..:.: :    *:::::...:*:* ***:****:***.

NTR1_RAT        MPVELYNFIWVHHPWAFGDAGCRGYYFLRDACTYATALNVASLSVERYLAICHPFKAKTL
PFI-002         MPLEVY-EMWRNYPFLFGPVGCYFKTALFETVCFASILSITTVSVERYVAILHPFRAKLQ
                **:*:* :*  ::*: **  .**   *  :: :*: *.::::*****:** ***:**

NTR1_RAT        MSRSRTKKFISAIWLASALLAIPMLFTMGLQN-RSGDG-THPGGLVCTPIVDTATVKVVI
PFI-002         STRRRALRILGIVWGFSVLFSLPNTSIHGIKFHYFPNGSLVPGSATCTVIKPMWIYNFII
                :* *: :::. :*  *.*::::*   *::  :*    :*  **. .** *    :..:*

NTR1_RAT        QVNTFMSFLFPMLVISILNTVIANKLTVMVHQAAEQGRVCTVGTHNGLEHSTFNMTIEPG
PFI-002         QVTSFLFYLLPMTVISVLYYLMALR-----------------------------------
                **.:*: :*:** ***.*   ::*  ;

NTR1_RAT        RVQALRHGVLVLRAVVIAFVVCWLPYHVRRLMFCYISDEQWTTFLFDFYHFYMLTNALF
PFI-002         ------------------------------------------------------------

NTR1_RAT        YVSSAINPILYNLVSANFRQVFLSTLACLCPGWRHRRKKRPTFSRKPNSMSSNHAFSTSA
PFI-002         ------------------------------------------------------------

NTR1_RAT        TRETLY
PFI-002         ------
```

Figure 4

```
CLUSTAL W (1.74) multiple sequence alignment

GPCR0244         -----MACNGS--AARGHFDP--EDLNLTDEALRLKYLGPQQTELFMPICATYLLIFVVG
GPCR0303         MAGMEKLQNASWIYQQKLEDPFQKHLNSTEEYLAF-LCGPRRSHFFLPVSVVYVPIFVVG
                      *.*    :   **  :.** *:* *  :    **::::.:*:*:...*: *****

GPCR0244         AVGNGLTCLVILRHKAMRTPTNYYLFSLAVSDLLVLLVGLPLELYEMWHNYPFLLGVGGC
GPCR0303         VIGNVLVCLVILQHQAMKTPTNYYLFSLAVSDLLVLLLGMPLEVYEMWRNYPFLFGPVGC
                 .:** *.***** :*:**:******************:*:*** ****:****:* **

GPCR0244         YFRTLLFEMVCLASVLNVTALSVERYVAVVHPLQARSMVTRAHVRRVLGAVWGLAMLCSL
GPCR0303         YFKTALFETVCFASILSITTVSVERYVAILHPFRAKLQSTRRRALRILGIVWGFSVLFSL
                 **:* *** **:**:*.:*:.:*******:.**::*:    **  :. *:** ***:::* **

GPCR0244         PNTSLHGIRQLHVPCRGPVPDSAVCMLVRPRALYNMVVQTTALLFFCLPMAIMSVLYLLI
GPCR0303         PNTSIHGIKFHYFPNGSLVPGSATCTVIKPMWIYNFIIQVTSFLFYLLPMTVISVLYYLM
                 ****:***:   :.*  .**.**.*  :::*   :**::*.*.::**. ***:::**** *:

GPCR0244         GLRLRRERLLLMQEAKGRGSAAARSRYTCRLQQHDRGRRQVTKMLFVLVVVFGICWAPFH
GPCR0303         ALRLKKDKSLEADE----GNANIQ-R-PC--------RKSVNKMLFVLVLVFAICWAPFH
                 .***::::  *   :*    *.*  : * .*       *:.:.*.******:** *******

GPCR0244         ADRVMWSVVSQWTDGLHLAFQHVHVISGIFFYLGSAANPVLYSLMSSRFRETFQEALC-L
GPCR0303         IDRLFFSFVEEWTESLAAVFNLVHVVSGVLFYLSSAVNPIIYNLLSRRFQAAFQNVISSF
                 **::.:*.*.:**:.*  .*: ***:**::***.**.**::*.*:*.**: :**:...:   :

GPCR0244         GACCH-----RLRPRHSSHSLSRMTTGSTLCDVG---SLGSWVH----PLAGNDGPEAQQ
GPCR0303         HKQWHSQHDPQLPPAQRNIFLTECHFVELTEDIGPQFLCQSSVHNSHLPTALSS-EQMSR
                       *     :* *   *:.   *:.    *:*      *  **    *  ..   : ..:

GPCR0244         ETDPS------
GPCR0303         TNYQSFHFNKT
                 .  *

GPCR0244 = NMUR1
GPCR0303 = Pfi002
```

Nucleotide sequence coding for PFI-002
SEQ ID NO: 1
ATGGAAAAACTTCAGAATGCTTCCTGGATCTACCAGCAGAAACTAGAAGATC
CATTCCAGAAACACCTGAACAGCACCGAGGAGTATCTGGCCTTCCTCTGCGG
ACCTCGGCGCAGCCACTTCTTCCTCCCCGTGTCTGTGGTGTATGTGCCAATTTT
TGTGGTGGGGGTCATTGGCAATGTCCTGGTGTGCCTGGTGATTCTGCAGCACC
AGGCTATGAAGACGCCCACCAACTACTACCTCTTCAGCCTGGCGGTCTCTGA
CCTCCTGGTCCTGCTCCTTGGAATGCCCCTGGAGGTCTATGAGATGTGGCGCA
ACTACCCTTTCTTGTTCGGGCCCGTGGGCTGCTACTTCAAGACGGCCCTCTTT
GAGACCGTGTGCTTCGCCTCCATCCTCAGCATCACCACCGTCAGCGTGGAGC
GCTACGTGGCCATCCTACACCCGTTCCGCGCCAAACTGCAGAGCACCCGGCG
CCGGGCCCTCAGGATCCTCGGCATCGTCTGGGGCTTCTCCGTGCTCTTCTCCC
TGCCCAACACCAGCATCCATGGCATCAAGTTCCACTACTTCCCCAATGGGTCC
CTGGTCCCAGGTTCGGCCACCTGTACGGTCATCAAGCCCATGTGGATCTACA
ATTTCATCATCCAGGTCACCTCCTTCCTATTCTACCTCCTCCCCATGACTGTCA
TCAGTGTCCTCTACTACCTCATGGCACTCAGAGTGAGTATCTAG

Figure 5B

Amino acid sequence coding for PFI-002

SEQ ID NO: 2
MEKLQNASWIYQQKLEDPFQKHLNSTEEYLAFLCGPRRSHFFLPVSVVYVPIFVV
GVIGNVLVCLVILQHQAMKTPTNYYLFSLAVSDLLVLLLGMPLEVYEMWRNYPF
LFGPVGCYFKTALFETVCFASILSITTVSVERYVAILHPFRAKLQSTRRRALRILGI
VWGFSVLFSLPNTSIHGIKFHYFPNGSLVPGSATCTVIKPMWIYNFIIQVTSFLFYL
LPMTVISVLYYLMALRVSI

Figure 6

SEQ ID NO: 3
ACCATGGCAGGGATGGAAAAACTT

SEQ ID NO: 4
GCTCTGAAAGAATTCAGGTTTTG

SEQ ID NO: 5
TCCAGAAACACCTGAACAGC

SEQ ID NO: 6
GAGGTAGAATAGGAAGGAGG

SEQUENCE LISTING

<160> NUMBER OF SEQ ID NOS: 6

<210> SEQ ID NO 1
<211> LENGTH: 729
<212> TYPE: DNA
<213> ORGANISM: Homo sapiens

<400> SEQUENCE: 1

```
atggaaaaac ttcagaatgc ttcctggatc taccagcaga aactagaaga tccattccag    60
aaacacctga acagcaccga ggagtatctg gccttcctct gcggacctcg gcgcagccac   120
ttcttcctcc ccgtgtctgt ggtgtatgtg ccaattttg tggtgggggt cattggcaat   180
gtcctggtgt gcctggtgat tctgcagcac caggctatga agacgcccac caactactac   240
ctcttcagcc tggcggtctc tgacctcctg gtcctgctcc ttggaatgcc cctggaggtc   300
tatgagatgt ggcgcaacta ccctttcttg ttcgggcccg tgggctgcta cttcaagacg   360
gccctctttg agaccgtgtg cttcgcctcc atcctcagca tcaccaccgt cagcgtggag   420
cgctacgtgg ccatcctaca cccgttccgc gccaaactgc agagcacccg gcgccgggcc   480
ctcaggatcc tcggcatcgt ctggggcttc tccgtgctct tctccctgcc caacaccagc   540
atccatggca tcaagttcca ctacttcccc aatgggtccc tggtcccagg ttcggccacc   600
tgtacggtca tcaagcccat gtggatctac aatttcatca tccaggtcac ctccttccta   660
ttctacctcc tccccatgac tgtcatcagt gtcctctact acctcatggc actcagagtg   720
agtatctag                                                           729
```

<210> SEQ ID NO 2
<211> LENGTH: 242
<212> TYPE: PRT
<213> ORGANISM: Homo sapiens

<400> SEQUENCE: 2

```
Met Glu Lys Leu Gln Asn Ala Ser Trp Ile Tyr Gln Gln Lys Leu Glu
 1               5                  10                  15

Asp Pro Phe Gln Lys His Leu Asn Ser Thr Glu Glu Tyr Leu Ala Phe
                20                  25                  30

Leu Cys Gly Pro Arg Arg Ser His Phe Phe Leu Pro Val Ser Val Val
            35                  40                  45

Tyr Val Pro Ile Phe Val Val Gly Val Ile Gly Asn Val Leu Val Cys
        50                  55                  60

Leu Val Ile Leu Gln His Gln Ala Met Lys Thr Pro Thr Asn Tyr Tyr
    65                  70                  75                  80

Leu Phe Ser Leu Ala Val Ser Asp Leu Leu Val Leu Leu Leu Gly Met
                85                  90                  95

Pro Leu Glu Val Tyr Glu Met Trp Arg Asn Tyr Pro Phe Leu Phe Gly
```

-continued

```
            100                 105                 110
Pro Val Gly Cys Tyr Phe Lys Thr Ala Leu Phe Glu Thr Val Cys Phe
        115                 120                 125

Ala Ser Ile Leu Ser Ile Thr Thr Val Ser Val Glu Arg Tyr Val Ala
130                 135                 140

Ile Leu His Pro Phe Arg Ala Lys Leu Gln Ser Thr Arg Arg Arg Ala
145                 150                 155                 160

Leu Arg Ile Leu Gly Ile Val Trp Gly Phe Ser Val Leu Phe Ser Leu
                165                 170                 175

Pro Asn Thr Ser Ile His Gly Ile Lys Phe His Tyr Phe Pro Asn Gly
            180                 185                 190

Ser Leu Val Pro Gly Ser Ala Thr Cys Thr Val Ile Lys Pro Met Trp
        195                 200                 205

Ile Tyr Asn Phe Ile Ile Gln Val Thr Ser Phe Leu Phe Tyr Leu Leu
    210                 215                 220

Pro Met Thr Val Ile Ser Val Leu Tyr Tyr Leu Met Ala Leu Arg Val
225                 230                 235                 240

Ser Ile

<210> SEQ ID NO 3
<211> LENGTH: 24
<212> TYPE: DNA
<213> ORGANISM: Homo sapiens

<400> SEQUENCE: 3
accatggcag ggatggaaaa actt                                              24

<210> SEQ ID NO 4
<211> LENGTH: 23
<212> TYPE: DNA
<213> ORGANISM: Homo sapiens

<400> SEQUENCE: 4
gctctgaaag aattcaggtt ttg                                               23

<210> SEQ ID NO 5
<211> LENGTH: 20
<212> TYPE: DNA
<213> ORGANISM: Homo sapiens

<400> SEQUENCE: 5
tccagaaaca cctgaacagc                                                   20

<210> SEQ ID NO 6
<211> LENGTH: 20
<212> TYPE: DNA
<213> ORGANISM: Homo sapiens

<400> SEQUENCE: 6
gaggtagaat aggaaggagg                                                   20
```

POLYNUCLEOTIDE ENCODING NEUROMEDIN U RECEPTOR

TECHNICAL FIELD

The present invention relates to a novel polynucleotide sequence which encodes a novel polypeptide belonging to the class of proteins known as G-protein coupled receptors (GPCRs). The present invention also relates, inter alia, to processes for producing the polypeptide and its uses.

BACKGROUND OF THE INVENTION

Cells and tissues respond to a wide variety of extracellular signalling molecules through the interaction of these molecules with specific cell-surface receptors. One such class of receptors are known as G-protein coupled receptors (GPCRs) and these are characterised by containing a series of 7 hydrophobic transmembrane segments. Upon binding an extracellular ligand to its receptor, intracellular signals are initiated via interactions with heterotrimeric G proteins which, in turn, can lead to a number of different intracellular events depending upon which receptor has been activated. For example some GPCRs influence adenyl cyclase activity whereas others act via phospholipase C.

Members of the GPCR superfamily respond to a wide variety of ligands including small molecule amines (such as serotonin, dopamine, acetylcholine), lipid-derived mediators (such as LpA), amino acid derivatives (such as glutamate) and neurotransmitter peptides and hormones (such as neurokinin, galanin, glucagon, gastrin). Although GPCRs are activated by a broad range of ligands, it should be noted that individual GPCRs have a small and very specific repertoire of ligands. Based upon an analysis of the primary structure of a novel GPCR, it is now possible to classify them into specific sub-families, thereby narrowing the range of potential ligands.

In many cases, the endogenous ligands of GPCRs are relatively small, enabling them to be mimicked or blocked by synthetic analogues. For example drugs such as prazosin, doxazosin, cimetidine, ranitidine are all effective antagonists of their respective target GPCRs.

Thus, as the modulation of GPCRs can have therapeutic consequences, there is a continued need to provide new GPCRs and their associated agonists and antagonists.

SUMMARY OF THE INVENTION

In a broad aspect, the present invention relates to novel amino acid sequences. In this regard, a specific novel amino acid sequence has been isolated and it is to be understood that the invention covers that sequence as well as novel variants, fragments, derivatives and homologues thereof.

In another broad aspect, the present invention relates to novel nucleic acid sequences. In this regard, a specific novel nucleic acid sequence has been isolated and it is to be understood that the invention covers that sequence as well as novel variants, fragments, derivatives and homologues thereof.

Thus, in brief, some aspects of the present invention relate to:
1. Novel amino acids.
2. Novel nucleotide sequences.
3. Assays using said novel sequences.
4. Compounds/compositions identified by use of said assays.
5. Expression systems comprising or expressing said novel sequences.
6. Methods of treatment based on said novel sequences.
7. Pharmaceutical compositions based on said novel sequences.

Other aspects concerning the amino acid sequence of the present invention and/or the nucleotide sequence of the present invention include: a construct comprising or capable of expressing the sequences of the present invention; a vector comprising or capable of expressing the sequences of the present invention; a plasmid comprising or capable of expressing the sequences of the present invention; a cell transfected or virally-transduced with a construct/vector/plasmid comprising or capable of expressing the sequences of the present invention; a tissue comprising or capable of expressing the sequences of the present invention; an organ comprising or capable of expressing the sequences of the present invention; a transformed host comprising or capable of expressing the sequences of the present invention; and a transformed organism comprising or capable of expressing the sequences of the present invention. The present invention also encompasses methods of expressing the same, such as expression in a micro-organism; including methods for transferring the same.

For ease of reference, aspects of the present invention are now discussed under appropriate section headings. However, the teachings under each section are not necessarily limited to each particular section.

In the following commentary references to "nucleotide sequence of the present invention" and "amino acid sequence of the present invention" refer respectively to any one or more of the nucleotide sequences presented or discussed herein and to any one or more of the amino acid sequences presented or discussed herein. Also, and as used herein, "amino acid sequence" refers to peptide or protein sequences and may refer to portions thereof. In addition, the term "amino acid sequence of the present invention" is synonymous with the phrase "polypeptide sequence of the present invention". Also, the term "nucleotide sequence of the present invention" is synonymous with the phrase "polynucleotide sequence of the present invention".

Other features and advantages of the invention will be apparent from the following detailed description and from the claims. While the invention is described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art. All publications mentioned herein are incorporated by reference in their entireties.

BRIEF DESCRIPTION OF THE DRAWINGS

FIG. 3 shows a ClustalW alignment of PFI-002 with SW|P20789|NTR1__RAT NEUROTENSIN RECEPTOR TYPE 1 (NT-R-1).

FIG. 4 shows a ClustalW alignment of PFI-002 with GB|AF044601|NMUR1__Human NEUROMEDIN RECEPTOR TYPE 1 (NMU-R-1).

FIG. 5A shows SEQ ID NO: 1, which is the nucleotide sequence coding for PFI-002. The ATG translation initiation codon is indicated by the first three letters. The stop codon is indicated by the last three letters.

FIG. 5B shows SEQ ID NO: 2 shows the corresponding amino acid sequence coding for PFI-002.

FIG. 6 shows SEQ ID NOS: 3–6 which are the various primers used throughout the Examples.

DETAILED DESCRIPTION

Figure 1:
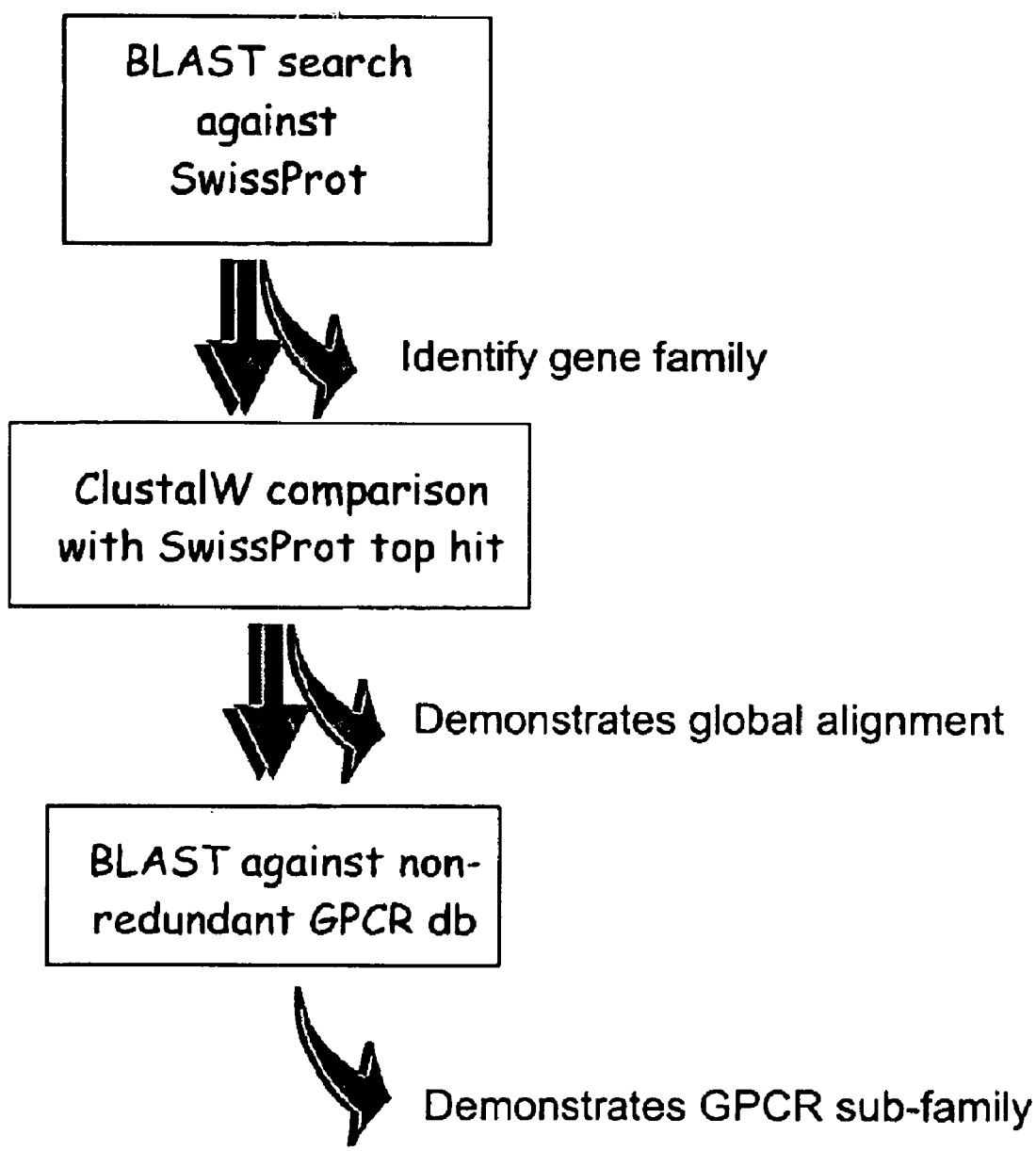
FIG. 1 shows a schema for the bioinformatic analysis of PFI-002 (db=database).

According to one aspect of the present invention, there is provided an isolated and/or purified polynucleotide comprising one or more of:

- (a) a polynucleotide encoding the polypeptide as set forth in SEQ ID NO: 2;
- (b) a polynucleotide comprising a nucleotide sequence of SEQ ID NO: 1;
- (c) a polynucleotide encoding the polypeptide expressed by the DNA contained in NCIMB 41066;
- (d) a polynucleotide comprising a nucleotide sequence that has at least 70% identity to the polynucleotide of any one of (a) to (c);
- (e) a polynucleotide comprising a nucleotide sequence which is capable of hybridising to the polynucleotide of any one of (a) to (d);
- (f) a complement to the polynucleotide of any one of (a) to (e); or
- (g) a polynucleotide fragment of the polynucleotide of any one of (a) to (f).

Preferably, the polynucleotide comprises a nucleotide sequence that has at least 75% identity to the polynucleotide of any one of (a) to (c). More preferably, the polynucleotide comprises a nucleotide sequence that has at least 80% identity to the polynucleotide of any one of (a) to (c). Even more preferably, the polynucleotide comprises a nucleotide sequence that has at least 85% identity to the polynucleotide of any one of (a) to (c). Yet more preferably, the polynucleotide comprises a nucleotide sequence that has at least 90% identity to the polynucleotide of any one of (a) to (c). More preferably, the polynucleotide comprises a nucleotide sequence that has at least 95% identity to the polynucleotide of any one of (a) to (c). Most preferably, the polynucleotide comprises a nucleotide sequence that has at least 98% identity to the polynucleotide of any one of (a) to (c).

The polynucleotide described above preferably encodes a G-protein coupled receptor (GPCR).

The present invention also provides a polynucleotide probe or primer comprising at least 15 contiguous nucleotides of the polynucleotide described above.

The present invention yet further provides a vector comprising the polynucleotide described above.

According to a further aspect of the present invention, there is provided a host cell transformed or transfected with the vector described above. Preferably, the host cell is a mammalian, insect, fungal, bacterial or yeast cell.

According to a further aspect of the present invention, there is provided the transcribed RNA product of the polynucleotide described above. There is also provided an RNA molecule or a fragment thereof which is antisense in relation to the RNA product and is capable of hybridising thereto.

There is yet further provided a ribozyme or zinc finger protein capable of binding to the polynucleotide described above.

According to yet a further aspect of the present invention, there is provided a process for producing a polypeptide or fragment thereof comprising culturing said host cell under conditions sufficient for the expression of said polypeptide or fragment. Preferably, said polypeptide or fragment is expressed at the surface of said cell. The process preferably further includes recovering the polypeptide or fragment from the culture.

There is also provided by the present invention a process for producing cells capable of expressing a polypeptide or fragment thereof comprising transforming or transfecting cells with the vector described above.

According to a further embodiment of the present invention, there are provided cells produced by the process described above. There is also provided a membrane preparation of said cells.

According to another aspect of the present invention, there is provided a polypeptide comprising:

- (a) a polypeptide having the deduced amino acid sequence translated from the polynucleotide sequence in SEQ ID NO: 1 and variants, fragments, homologues, analogues and derivatives thereof;
- (b) a polypeptide of SEQ ID NO: 2 and variants, fragments, homologues, analogues and derivatives thereof; or
- (c) a polypeptide encoded by the cDNA of NCIMB 41066 and variants, fragments, homologues, analogues and derivatives thereof.

There is also provided by the present invention an antibody against the polypeptide described above.

The present invention yet further provides a compound, which modulates the polypeptide described above. Preferably, the compound antagonises or selectively antagonises the polypeptide. Alternatively, the compound agonises the polypeptide.

Also provided by the present invention is a pharmaceutical composition comprising the antibody or compound described above and one or more pharmaceutically acceptable carriers, diluents, adjuvants or excipients.

According to another aspect of the present invention, there is provided a method for identifying a compound, which binds to and modulates the polypeptide described above comprising contacting said polypeptide with a candidate compound and determining whether modulation occurs.

Preferably, said method comprises:

- (a) contacting a compound with cells expressing the polypeptide described above on their cell surface, said polypeptide being associated with a second component capable of providing a detectable signal in response to the binding of a compound to said polypeptide; said contacting being under conditions sufficient to permit binding of compounds to the polypeptide; and
- (b) identifying a compound capable of polypeptide binding by detecting the signal produced by said second component.

Alternatively, said method comprises:

- (a) contacting (i) a detectable first component known to bind to the polypeptide described above and (ii) a compound, with cells expressing the above polypeptide on their cell surface, said polypeptide being associated with a second component capable of providing a detectable signal in response to the binding of a compound to said polypeptide; said contacting being under conditions sufficient to permit binding of compounds to the polypeptide; and
- (b) determining whether the first component binds to the polypeptide by detecting the absence or otherwise of a signal generated from the interaction of the first component with the polypeptide.

The compound identified by any of the above methods preferably binds to and (i) antagonises or selectively antagonises the polypeptide described above, or (ii) agonises the polypeptide described above.

As GPCRs are involved in signal transduction, modulators (e.g. agonists or antagonists) of the polypeptide of the present invention can find use in interfering in the signal transduction process.

Therefore, according to yet another embodiment of the present invention, there is provided the antibody, compound or composition described above for use as a pharmaceutical.

Such antibodies, compounds and compositions, which can modulate the polypeptide of the present invention, can therefore find use in the therapeutic areas which concern aspects of signal transduction. Therapeutically usefully areas include, but are not limited to, obesity, diabetes and metabolic disease, neurological disease, psychotherapeutics, urogenital disease. reproduction and sexual medicine, inflammation, cancer, tissue repair, dermatology, skin pigmentation, photoaging, frailty, osteoporosis, cardiovascular disease, gastrointestinal disease, antiinfection, allergy and respiratory disease, sensory organ disorders, sleep disorders and hairloss.

Accordingly, there is also provided the use of the compound described above in the manufacture of a medicament for the treatment of a patient having need to modulate the polypeptide described above. Preferably, the treatment is for a patient having need to antagonise or selectively antagonise the polypeptide. Alternatively, the treatment is for a patient having need to agonise the polypeptide.

According to yet a further aspect of the invention, there is provided a method for the treatment of a patient having need to modulate the polypeptide described above comprising administering to the patient a therapeutically effective amount of the above-described compound. Preferably, said method is for the treatment of a patient having need to antagonise or selectively antagonise the polypeptide. Alternatively, said method is for the treatment of a patient having need to agonise the polypeptide.

Preferably, said compound is a polypeptide and a therapeutically effective amount of the compound is administered by providing to the patient DNA encoding said compound and expressing said compound in vivo.

There is also provided by the present invention use of the antibody described above in the manufacture of a medicament for the treatment of a patient having need to modulate the polypeptide described above. Preferably, said method is for the treatment of a patient having need to antagonise or selectively antagonise the polypeptide. Alternatively, said method is for the treatment of a patient having need to agonise the polypeptide.

Yet further provided by the present invention is a method for the treatment of a patient having need to modulate the polypeptide described above, comprising administering to the patient a therapeutically effective amount of the antibody described above. Preferably, said method is for the treatment of a patient having need to antagonise or selectively antagonise the polypeptide. Alternatively, said method is for the treatment of a patient having need to agonise the polypeptide.

The present invention also provides use of the compound described above in the manufacture of a medicament for the treatment of obesity.

Yet further provided by the present invention is use of the antibody described above in the manufacture of a medicament for the treatment of obesity.

The present invention also provides a method for the treatment of obesity in a patient comprising administering to the patient a therapeutically effective amount of the compound described above.

Yet further provided by the present invention is a method for the treatment of obesity in a patient comprising administering to the patient a therapeutically effective amount of the antibody described above.

According to yet a further aspect of the present invention, there are provided cells genetically engineered ex vivo or in vivo to express, overexpress, underexpress or to exhibit targeted insertion or deletion of the polypeptide of the present invention.

PFI-002 POLYPEPTIDE

As explained above, the present invention relates to a novel GPCR—which has been internally designated PFI-002—and to a nucleotide sequence encoding same. The present invention also relates to the use of the novel nucleic acid and amino acid sequences in the diagnosis and treatment of disease. The present invention also relates to the use of the novel nucleic acid and amino acid sequences to evaluate and/or to screen for agents that can modulate the GPCR. The present invention further relates to genetically engineered host cells that comprise or express the novel nucleic acid and amino acid sequences to evaluate and/or to screen for agents that can modulate the GPCR.

The PFI-002 polypeptide may be the same as the naturally occurring form—for this aspect, preferably the PFI-002 polypeptide is the non-native amino acid sequence (i.e. it is not present in its natural environment)—or is a variant, homologue, fragment or derivative thereof. In addition, or in the alternative, the PFI-002 polypeptide is isolated PFI-002 polypeptide and/or purified PFI-002 polypeptide. The PFI-002 polypeptide can be obtainable from or produced by any suitable source, whether natural or not, or it may be synthetic, semi-synthetic or recombinant.

The PFI-002 coding sequence may be the same as the naturally occurring form—for this aspect, preferably the PFI-002 coding sequence is the non-native nucleotide sequence (i.e. it is not present in its natural environment)—or is a variant, homologue, fragment or derivative thereof. In addition, or in the alternative, the PFI-002 coding sequence is an isolated PFI-002 coding sequence and/or a purified PFI-002 coding sequence. The PFI-002 coding sequence can be obtainable from or produced by any suitable source, whether natural or not, or it may be synthetic, semi-synthetic or recombinant.

PFI-002 POLYPEPTIDE AND SCREENING

The PFI-002 polypeptide and/or its coding sequence and/or a sequence capable of hybridising thereto is/are useful for testing the selectivity of drug candidates between different GPCRS.

It has been demonstrated (herein) that PFI-002 is most closely similar to neurotensin receptors and that PFI-002 encodes a novel GPCR whose ligand is likely to be a peptide.

Drugs that modulate the novel PFI-002 receptor will therefore be likely to modulate signal transduction processes. It is therefore likely that modulators of the PFI-002 receptor may be useful for the treatment of many different disorders associated with signal transduction that will most likely include, but is not limited to, obesity, diabetes and metabolic disease, neurological disease, psychotherapeutics, urogenital disease, reproduction and sexual medicine, inflammation, cancer, tissue repair, dermatology, skin pigmentation, photoaging, frailty, osteoporosis, cardiovascular disease, gastrointestinal disease, antinfection, allergy and respiratory disease, sensory organ disorders, sleep disorders and hairloss.

Thus, the PFI-002 polypeptide and/or its coding sequence and/or a sequence capable of hybridising thereto may be useful for screening drug candidates for the treatment of diseases associated with signal transduction. In addition, it is believed that PFI-002 polypeptide and/or its coding sequence and/or a sequence capable of hybridising thereto may be useful for screening drug candidates for the treatment of diseases such as those described above.

Either or both of the nucleotide sequences coding for the PFI-002 polypeptide or the PFI-002 polypeptide itself may be used to screen for agents that can affect GPCR activity. In particular, the nucleotide sequence coding for the PFI-002 receptor itself may be used to screen for agents that can antagonise GPCR activity. In addition, the nucleotide sequence coding for PFI-002 polypeptide or the PFI-002 polypeptide itself may be used to screen for agents that selectively affect GPCR activity, such as selectively antagonise the PFI-002 receptor.

POLYPEPTIDE OF THE PRESENT INVENTION

The term "polypeptide"—which is interchangeable with the term "proteins—includes single-chain polypeptide molecules as well as multiple-polypeptide complexes where individual constituent polypeptides are linked by covalent or non-covalent means.

Preferably, the polypeptide of the present invention is a single-chain polypeptide.

Polypeptides of the present invention may be in a substantially isolated form. It will be understood that the polypeptide may be mixed with carriers or diluents which will not interfere with the intended purpose of the polypeptide and still be regarded as substantially isolated. A polypeptide of the present invention may also be in a substantially purified form, in which case it will generally comprise the polypeptide in a preparation in which more than 90%, e.g. 95%, 98% or 99% of the polypeptide in the preparation is a polypeptide of the present invention. Polypeptides of the present invention may be modified for example by the addition of histidine residues to assist their purification.

Polypeptides of the present invention may be produced by synthetic means (e.g. as described by Geysen et al., 1996) or recombinantly, as described below.

In a preferred embodiment, the amino acid sequence per se of the present invention does not cover the native PFI-002 receptor according to the present invention when it is in its natural environment and when it has been expressed by its native nucleotide coding sequence which is also in its natural environment and when that nucleotide sequence is under the control of its native promoter which is also in its natural environment. For ease of reference, we have called this preferred embodiment the "non-native amino acid sequence".

The terms "variant", "homologue", "fragment", "analogue" or "derivative" in relation to the amino acid sequence for the polypeptide of the present invention include any substitution of, variation of, modification of, replacement of, deletion of or addition of one (or more) amino acid from or to the sequence providing the resultant polypeptide has GPCR activity, preferably being at least as biologically active as the polypeptide shown in attached SEQ ID NO: 2.

In particular, the term "homologue" covers homology with respect to structure and/or function. With respect to sequence homology, there is at least 70%, preferably at least 75%, more preferably at least 80%, more preferably at least 85%, more preferably at least 90%, more preferably at least 95% homology to the sequence shown in SEQ ID NO: 2. Most preferably there is at least 98% homology to the sequence shown in SEQ ID NO: 2.

Typically, for the variant, homologue or fragment of the present invention, the types of amino acid substitutions that could be made should maintain the hydrophobicity/hydrophilicity of the amino acid sequence. Amino acid substitutions may be made, for example from 1, 2 or 3 to 10, 20 or 30 substitutions provided that the modified sequence retains the ability to act as a GPCR in accordance with the present invention. Amino acid substitutions may include the use of non-naturally occurring analogues.

The amino acid sequence of the present invention may be produced by expression of a nucleotide sequence coding for same in a suitable expression system.

In addition, or in the alternative, the protein itself could be produced using chemical methods to synthesize a PFI-002 polypeptide, in whole or in part. For example, peptides can be synthesized by solid phase techniques, cleaved from the resin, and purified by preparative high performance liquid chromatography (e.g. Creighton (1983) Proteins Structures and Molecular Principles, WH Freeman and Co., New York, N.Y., USA). The composition of the synthetic peptides may be confirmed by amino acid analysis or sequencing (e.g. the Edman degradation procedure).

Direct peptide synthesis can be performed using various solid-phase techniques (Roberge J Y et al Science Vol 269 1995 202–204) and automated synthesis may be achieved, for example, using the ABI 431 A Peptide Synthesizer (Perkin Elmer) in accordance with the instructions provided by the manufacturer. Additionally, the amino acid sequence of PFI-002, or any part thereof, may be altered during direct synthesis and/or combined using chemical methods with a sequence from other subunits, or any part thereof, to produce a variant polypeptide.

In another embodiment of the invention, a PFI-002 natural, modified or recombinant amino acid sequence may be ligated to a heterologous sequence to encode a fusion protein. For example, for screening of libraries for compounds and peptide agonists and antagonists of PFI-002 GPCR activity, it may be useful to encode a chimeric PFI-002 protein expressing a heterologous epitope that is recognised by a commercially available antibody. A fusion protein may also be engineered to contain a cleavage site located between a PFI-002 sequence and the heterologous protein sequence, so that the PFI-002 may be cleaved and purified away from the heterologous moiety.

PFI-002 may also be expressed as a recombinant protein with one or more additional polypeptide domains added to facilitate protein purification. Such purification facilitating domains include, but are not limited to, metal chelating peptides such as histidine-tryptophan modules that allow purification on immobilised metals (Porath J, Protein Expr Purif Vol 3 1992 p263–281), protein A domains that allow purification on immobilised immunoglobulin, and the domain utilised in the FLAGS extension/affinity purification system (Immunex Corp, Seattle, Wash., USA). The inclusion of a cleavable linker sequence such as Factor XA or enterokinase (Invitrogen, San Diego, Calif., USA) between the purification domain and PFI-002 is useful to facilitate purification.

A specific amino acid sequence of PFI-002 is shown in SEQ ID NO: 2. However, the present invention encompasses amino acid sequences encoding other GPCRs which would include amino acid sequences having at least 70% identity (preferably at least 75%, more preferably at least 80%, more preferably at least 85%, more preferably at least 90%, more preferably at least 95%, most preferably at least 98% identity) to that specific amino acid sequence.

Polypeptides of the present invention also include fragments of the present amino acid sequence and variants thereof. Suitable fragments will be at least 5, e.g. at least 10, 12, 15 or 20 amino acids in size.

Polypeptides of the present invention may also be modified to contain one or more (e.g. at least 2, 3, 5, or 10) substitutions, deletions or insertions, including conserved substitutions. These aspects are discussed in a later section.

NUCLEOTIDE SEQUENCE OF THE PRESENT INVENTION

The term "nucleotide sequence" as used herein refers to an oligonucleotide sequence or polynucleotide sequence, and variants, homologues, fragments, analogues and derivatives thereof (such as portions thereof). The nucleotide sequence may be DNA or RNA which may be of genomic or synthetic or recombinant origin which may be double-stranded or single-stranded whether representing the sense or antisense strand.

Preferably, the term "nucleotide sequence" means DNA.

More preferably, the term "nucleotide sequence" means DNA prepared by use of recombinant DNA techniques (i.e. recombinant DNA).

In a preferred embodiment, the nucleotide sequence per se of the present invention does not cover the native nucleotide coding sequence according to the present invention in its natural environment when it is under the control of its native promoter which is also in its natural environment. For ease of reference, we have called this preferred embodiment the "non-native nucleotide sequence".

The nucleotide sequences of the present invention may include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the nucleotide sequences described herein may be modified by any method available in the art. Such modifications may be carried out in to enhance the in vivo activity or life span of nucleotide sequences of the present invention.

The present invention also encompasses nucleotide sequences that are complementary to the sequences presented herein, or any variant, homologue, analogue, fragment or derivative thereof. If the sequence is complementary to a fragment thereof then that sequence can be used a probe to identify similar coding sequences in other organisms, etc.

The present invention also encompasses nucleotide sequences that are capable of hybridising to the sequences presented herein, or any variant, homologue, analogue, fragment or derivative thereof.

The present invention also encompasses nucleotide sequences that are capable of hybridising to the sequences that are complementary to the sequences presented herein, or any variant, homologue, analogue, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 65° C. and 0.1×SSC {1×SSC=0.15 M NaCl, 0.015 $Na_3$ citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 65° C. and 0.1× SSC).

Exemplary nucleic acids can alternatively be characterised as those nucleotide sequences which encode a PFI-002 protein and hybridise to the DNA sequence shown in SEQ ID NO: 1. Preferred are such sequences encoding PFI-002 which hybridise under high-stringency conditions to the sequence shown in SEQ ID NO: 1 or the complement thereof.

Advantageously, the invention provides nucleic acid sequences which are capable of hybridising, under stringent conditions, to a fragment of the sequence shown in the SEQ ID NO:1 or the complement thereof. Preferably, the fragment is between 15 and 50 bases in length. Advantageously, it is about 25 bases in length.

The terms "variant", "homologue", "analogue", "derivative" or "fragment" in relation to the nucleotide sequence coding for the preferred polypeptide of the present invention include any substitution of, variation of, modification of, replacement of, deletion of or addition of one (or more) nucleic acid from or to the sequence providing the resultant nucleotide sequence codes for or is capable of coding for an polypeptide having PFI-002 receptor activity, preferably being at least as biologically active as the polypeptide encoded by the sequence shown in SEQ ID NO: 1. In particular, the term "homologue" covers homology with respect to structure and/or function providing the resultant nucleotide sequence codes for or is capable of coding for a polypeptide having activity as a PFI-002 GPCR. With respect to sequence homology, preferably there is at least 70%, preferably at least 75%, more preferably at least 80%, more preferably at least 85%, more preferably at least 90%, more preferably at least 95% homology to a nucleotide sequence coding for the amino acid sequence shown in SEQ ID NO: 2. Most preferably there is at least 98% homology to a nucleotide sequence coding for the amino acid sequence shown in SEQ ID NO: 2. With respect to sequence homology, there is at least 70%, preferably at least 75%, more preferably at least 80%, more preferably at least 85%, more preferably at least 90%, more preferably at least 95% homology to the nucleotide sequence shown in SEQ ID NO: 1. Most preferably there is at least 98% homology to the nucleotide sequence shown in SEQ ID NO: 1.

As indicated, the present invention relates to a DNA sequence (preferably a cDNA sequence) encoding PFI-002. In particular, the present invention relates to cDNA sequences encoding PFI-002.

The present invention also relates to DNA segments comprising the DNA sequence shown in SEQ ID NO: 1 or allelic variations thereof.

The present invention also relates to polypeptides produced by expression in a host cell into which has been incorporated the foregoing DNA sequences or allelic variations thereof.

The present invention also relates provides DNA comprising the DNA sequence shown in SEQ ID NO: 1 or allelic variations thereof.

The present invention also relates to non-native DNA comprising the DNA sequence shown in SEQ ID NO: 1 or allelic variations thereof.

A highly preferred aspect of the present invention relates to recombinant DNA comprising the DNA sequence shown in SEQ ID NO: 1 or allelic variations thereof.

Polynucleotides of the present invention include nucleic acid sequences encoding the polypeptides of the present invention. It will be appreciated that a range of different polynucleotides encode a given amino acid sequence as a consequence of the degeneracy of the genetic code.

By knowledge of the amino acid sequences set out herein it is possible to devise partial and full-length nucleic acid sequences such as cDNA and/or genomic clones that encode the polypeptides of the present invention. For example, polynucleotides of the present invention may be obtained using degenerate polymerase chain reaction (PCR) which will use primers designed to target sequences encoding the amino acid sequences presented herein. The primers will typically contain multiple degenerate positions. However, to minimise degeneracy, sequences will be chosen that encode regions of the amino acid sequences presented herein containing amino acids such as methionine which are coded for by only one triplet. In addition, sequences will be chosen to take into account codon usage in the organism whose nucleic acid is used as the template DNA for the PCR procedure. PCR will be used at stringency conditions lower than those used for cloning sequences with single sequence (non-degenerate) primers against known sequences.

Nucleic acid sequences obtained by PCR that encode polypeptide fragments of the present invention may then be used to obtain larger sequences using hybridisation library screening techniques. For example a PCR clone may be labelled with radioactive atoms and used to screen a cDNA or genomic library from other species, preferably other mammalian species. Hybridisation conditions will typically be conditions of medium to high stringency (for example 0.03M sodium chloride and 0.03M sodium citrate at from about 50° C. to about 60° C.).

Degenerate nucleic acid probes encoding all or part of the amino acid sequence may also be used to probe cDNA and/or genomic libraries from other species, preferably other mammalian species. However, it is preferred to carry out PCR techniques initially to obtain a single sequence for use in further screening procedures.

In accordance with the present invention, polynucleotide sequences which encode PFI-002, fragments of the polypeptide, fusion proteins or functional equivalents thereof, may be used to generate recombinant DNA molecules that direct the expression of PFI-002 in appropriate host cells. Due to the inherent degeneracy of the genetic code, other DNA sequences which encode substantially the same or a functionally equivalent amino acid sequence, may be used to clone and express PFI-002. As will be understood by those of skill in the art, it may be advantageous to produce PFI-002-encoding nucleotide sequences possessing non-naturally occurring codons. Codons preferred by a particular procaryotic or eukaryotic host (Murray E et al (1989) Nuc Acids Res 17:477–508) can be selected, for example, to increase the rate of PFI-002 expression or to produce recombinant RNA transcripts having desirable properties, such as a longer half-life, than transcripts produced from naturally occurring sequence.

Polynucleotide sequences of the present invention obtained using the techniques described above may be used to obtain further homologous sequences and variants using the techniques described above. They may also be modified for use in expressing the polypeptides of the present invention in a variety of host cells systems, for example to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Altered PFI-002 polynucleotide sequences which may be used in accordance with the invention include deletions, insertions or substitutions of different nucleotide residues resulting in a polynucleotide that encodes the same or a functionally equivalent PFI-002. The protein may also have deletions, insertions or substitutions of amino acid residues which produce a silent change and result in a functionally equivalent PFI-002. Deliberate amino acid substitutions may be made on the basis of similarity in polarity, charge, solubility, hydrophobicity, hydrophilicity, and/or the amphipathic nature of the residues as long as the biological activity of PFI-002 is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Included within the scope of the present invention are alleles of PFI-002. As used herein, an "allele" or "allelic sequence" is an alternative form of PFI-002. Alleles result from a mutation, i.e. a change in the nucleic acid sequence, and generally produce altered mRNAs. or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a PFI-002 coding sequence for a variety of reasons, including but not limited to, alterations which modify the cloning, processing and/or expression of the gene product. For example, mutations may be introduced using techniques which are well known in the art, e.g. site-directed mutagenesis to insert new restriction sites, to alter glycosylation patterns or to change codon preference.

Polynucleotides of the present invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the present invention as used herein.

Polynucleotides or primers of the present invention may carry a revealing label. Suitable labels include radioisotopes such as $^{32}$P or $^{35}$S, enzyme labels, or other protein labels such as biotin. Such labels may be added to polynucleotides or primers of the present invention and may be detected using by techniques known in the art.

Polynucleotides such as a DNA polynucleotide and primers according to the present invention may be produced recombinantly, synthetically, or by any means available to those of skill in the art. They may also be cloned by standard techniques.

In general, primers will be produced by synthetic means, involving a step-wise manufacture of the desired nucleic acid sequence one nucleotide at a time. Techniques for accomplishing this using automated techniques are readily available in the art.

Longer polynucleotides will generally be produced using recombinant means, for example using PCR cloning techniques. This will involve making a pair of primers (e.g. of about 15–30 nucleotides) to a region of the nucleotide sequence which it is desired to clone, bringing the primers into contact with mRNA or cDNA obtained from a eukaryotic or prokaryotic cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

As mentioned earlier, the present invention also relates to nucleotide sequences that are capable of hybridising to all or part of the sequence shown in SEQ ID NO: 1 or an allelic variation thereof. These nucleotide sequences may be used in antisense techniques to modify PFI-002 expression. Alternatively, these sequences (or portions thereof) can be used as a probe, or for amplifying all or part of such sequence when used as a PCR primer.

In addition to the recombinant DNA sequences, genomic sequences are also of utility in the context of drug discovery. It may be valuable to inhibit the mRNA transcription of a particular isoform rather than to inhibit its translated protein. This may be true with PFI-002, if there are splice variants and wherein those different splice variants may be transcribed from different promoters.

Another utility of the invention is that the DNA sequences, once known, give the information needed to design assays to specifically detect isoforms or splice variants. Isoform-specific PCR primer pairs are but one example of an assay that depends completely on the knowledge of the specific DNA sequence of the isoform or splice variant. Such an assay allows detection of mRNA for the isoform to access the tissue distribution and biological relevance of each isoform to a particular disease state. It also allows identification of cell lines that may naturally express only one isoform—a discovery that might obviate the need to express recombinant genes. If specific PFI-002 isoforms are shown to be associated with a particular disease state, the invention would be valuable in the design of diagnostic assays to detect the presence of isoform mRNA.

An abnormal level of nucleotide sequences encoding a PFI-002 receptor in a biological sample may reflect a chromosomal aberration, such as a nucleic acid deletion or mutation. Accordingly, nucleotide sequences encoding a PFI-002 receptor provide the basis for probes which can be used diagnostically to detect chromosomal aberrations such as deletions, mutations or chromosomal translocations in the gene encoding PFI-002. PFI-002 gene expression may be altered in such disease states or there may be a chromosomal aberration present in the region of the gene encoding PFI-002.

In an alternative embodiment of the invention, the coding sequence of PFI-002 could be synthesized, in whole or in part, using chemical methods well known in the art (see Caruthers M H et al (1980) Nuc Acids Res Symp Ser 215–23, Horn T et al (1980) Nuc Acids Res Symp Ser 225–232).

NATURALLY OCCURRING

As used herein "naturally occurring" refers to a PFI-002 with an amino acid sequence found in nature.

ISOLATED/PURIFIED

As used herein, the terms "isolated" and "purified" refer to molecules, either nucleic or amino acid sequences, that are removed from their natural environment and isolated or separated from at least one other component with which they are naturally associated.

BIOLOGICALLY ACTIVE

As used herein "biologically active" refers to a PFI-002 according to the present invention—such as a recombinant PFI-002—having a similar structural function (but not necessarily to the same degree), and/or similar regulatory function (but not necessarily to the same degree), and/or similar biochemical function (but not necessarily to the same degree) and/or immunological activity (but not necessarily to the same degree) of the naturally occurring PFI-002. Specifically, a PFI-002 of the present invention has the ability to act as a GPCR, which is one of the characteristic activities of the PFI-002 polypeptide of the present invention.

IMMUNOLOGICAL ACTIVITY

As used herein, "immunological activity" is defined as the capability of the natural, recombinant or synthetic PFI-002 or any oligopeptide thereof, to induce a specific immune response in appropriate animals or cells and to bind with specific antibodies.

DERIVATIVE

The term "derivative" as used herein in relation to the amino acid sequence includes chemical modification of a PFI-002. Illustrative of such modifications would be replacement of hydrogen by an alkyl, acyl, or amino group.

ANALOGUE

The term "analogue" as used herein in relation to the amino acid sequence (or the coding sequence thereof)

includes chemical modification of a PFI-002 or the coding sequence thereof. Illustrative of such modifications would be replacement of natural amino acid residues or natural nucleotides with non-natural amino acid residues (e.g. D-amino acids, beta-alanine, hydroxyproline) or non-natural nucleotides (e.g. inosine, demethyl-cytidine).

DELETION

As used herein a "deletion" is defined as a change in either nucleotide or amino acid sequence in which one or more nucleotides or amino acid residues, respectively, are absent.

INSERTION/ADDITION

As used herein an "insertion" or "addition" is a change in a nucleotide or amino acid sequence which has resulted in the addition of one or more nucleotides or amino acid residues, respectively, as compared to the naturally occurring PFI-002.

SUBSTITUTION

As used herein "substitution" results from the replacement of one or more nucleotides or amino acids by different nucleotides or amino acids, respectively.

HOMOLOGUE

The term "homologue" with respect to the nucleotide sequence of the present invention and the amino acid sequence of the present invention may be synonymous with allelic variations of the sequences.

In particular, the term "homology" as used herein may be equated with the term "identity". Here, sequence homology with respect to the nucleotide sequence of the present invention and the amino acid sequence of the present invention can be determined by a simple "eyeball" comparison (i.e. a strict comparison) of any one or more of the sequences with another sequence to see if that other sequence has at least 70% identity to the nucleotide and amino acid sequences. Relative sequence homology (i.e. sequence identity) can also be determined by commercially available computer programs that can calculate percentage (%) homology between two or more sequences. Typical examples of such computer programs are FASTA or BLAST.

Percentage (%) homology may be calculated over contiguous sequences, i.e. one sequence is aligned with the other sequence and each amino add in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Altschul et al., 1990, J. Mol. Biol., 403–410) and the GENEWORKS suite of comparison tools. Both BLAST and FASTA are available for off-line and on-line searching (see Ausubel et al., 1999 ibid, pages 7–58 to 7–60). However, for some applications it is preferred to use the GCG Bestfit program.

Although the final % homology can be measured in terms of identity, in some cases, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

As indicated, for some applications, sequence homology (or identity) may be determined using any suitable homology algorithm, using for example default parameters. For a discussion of basic issues in similarity searching of sequence databases, see Altschul, et al (1994) Nature Genetics 6:119–129. For some applications, the BLAST algorithm is employed, with parameters set to default values. The BLAST algorithm is described in detail at the NCBI database. Advantageously, "substantial homology", when assessed by BLAST, equates to sequences which match with an EXCEPT value of at least e-7, preferably about e-9 and most preferably e-10 or lower. The defaulted threshold for EXCEPT in BLAST searching is usually 10.

Should Gap Penalties be used when determining sequence identity, then preferably the following parameters are used:

| FOR BLAST | | |
| --- | --- | --- |
| GAP OPEN | 5 | |
| GAP EXTENSION | 2 | |

| FOR CLUSTAL | DNA | PROTEIN | |
| --- | --- | --- | --- |
| WORD SIZE | 2 | 1 | K triple |
| GAP PENALTY | 10 | 10 | |
| GAP EXTENSION | 0.1 | 0.1 | |

Other computer program methods to determine identity and similarity between the two sequences include but are not limited to the GCG program package (Devereux et al., 1984 Nucleic Acids Research 12: 387) and FASTA (Altschul et al 1990 J Molec Biol 403–410).

POLYPEPTIDE VARIANTS AND DERIVATIVES

The terms "variant" or "derivative" in relation to the amino acid sequences of the present invention includes any substitution of, variation of, modification of, replacement of, deletion of or addition of one (or more) amino acids from or to the sequence providing the resultant amino add sequence has PFI-002 activity, preferably having at least the same activity as the polypeptide presented in SEQ ID NO: 2.

The sequences of the present invention may be modified for use in the present invention. Typically, modifications are made that maintain the PFI-002 activity of the sequence. Amino acid substitutions may be made, for example from 1, 2 or 3 to 10, 20 or 30 substitutions provided that the modified sequence retains PFI-002 activity. Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |

As indicated above, proteins of the invention are typically made by recombinant means, for example as described herein, and/or by using synthetic means using techniques well known to the skilled person such as solid phase synthesis. Variants and derivatives of such sequences include fusion proteins, wherein the fusion proteins comprise at least the amino acid sequence of the present invention being linked (directly or indirectly) to another amino acid sequence. These other amino acid sequences—which are sometimes referred to as fusion protein partners—will typically impart a favourable functionality—such as to aid extraction and purification of the amino acid sequence of the present invention. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of the present invention so as to allow removal of the latter. Preferably the fusion protein partner will not hinder the function of the protein of the present invention.

POLYNUCLEOTIDE VARIANTS AND DERIVATIVES

The terms "variant" or "derivative" in relation to the nucleotide sequence of the present invention include any substitution of, variation of, modification of, replacement of, deletion of or addition of one (or more) nucleic acid from or to the sequence providing the resultant nucleotide sequence codes for a polypeptide having PFI-002 activity, preferably having at least the same activity as the sequence presented in SEQ ID NO: 2.

As indicated above, with respect to sequence homology, there is at least 70%, preferably at least 75%, more preferably at least 80%, more preferably at least 85%, more preferably at least 90%, more preferably at least 95% homology to the nucleotide sequence shown in SEQ ID NO: 1. Most preferably there is at least 98% homology to the nucleotide sequence shown in SEQ ID NO: 1. Nucleotide homology comparisons may be conducted as described above. For some applications, a preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

As used herein, the terms "variant", "homologue", "fragment" and derivative" embrace allelic variations of the sequences.

The term "variant" also encompasses sequences that are complementary to sequences that are capable of hydridising to the nucleotide sequences presented herein.

HYBRIDISATION

The term "hybridisation" as used herein shall include "the process by which a strand of nucleic acid joins with a complementary strand through base pairing" (Coombs J (1994) Dictionary of Biotechnology, Stockton Press, New York, N.Y., USA) as well as the process of amplification as carried out in PCR technologies as described in Dieffenbach C W and G S Dveksler (1995, PCR Primer, a Laboratory Manual, Cold Spring Harbor Press, Plainview, N.Y., USA).

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego, Calif., USA), and confer a defined "stringency" as explained below.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M $Na^+$ at 65–68° C.

Maximum stringency typically occurs at about Tm-5° C. (5° C. below the Tm of the probe).

High stringency occurs at about 5° C. to 10° C. below the Tm of the probe. High stringency conditions can be provided, for example, by hybridisation in an aqueous solution containing 6×SSC, 5×Denhardt's, 1% SDS (sodium dodecyl sulphate), 0.1 Na$^+$ pyrophosphate and 0.1 mg/ml denatured salmon sperm DNA as non-specific competitor. Following hybridisation, high stringency washing may be done in several steps, with a final wash (about 30 min) at the hybridisation temperature in 0.2–0.1×SSC, 0.1% SDS.

Moderate, or intermediate, stringency typically occurs at about 10° C. to 20° C. below the Tm of the probe.

Low stringency typically occurs at about 20° C. to 25° C. below the Tm of the probe.

As will be understood by those of skill in the art, a maximum stringency hybridisation can be used to identify or detect identical polynucleotide sequences while an intermediate (or low) stringency hybridisation can be used to identify or detect similar or related polynucleotide sequences.

Moderate stringency refers to conditions equivalent to hybridisation in the above-described solution but at about 60–62° C. In that case the final wash is performed at the hybridisation temperature in 1×SSC, 0.1% SDS.

Low stringency refers to conditions equivalent to hybridisation in the above-described solution at about 50–52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g., Sambrook, et al., eds. (1989) Molecular Cloning: A Laboratory Manual, Cold Spring Harbor Laboratory Press, New York, N.Y., USA or Ausubel, et al., eds. (1990) Current Protocols in Molecular Biology, John Wiley & Sons, Inc.). Optimal hybridisation conditions have to be determined empirically, as the length and the GC content of the probe also play a role.

Polynucleotides of the invention capable of selectively hybridising to the nucleotide sequences presented herein, or to their complement, will be generally at least 70%, preferably at least 75%, more preferably at least 80%, more preferably at least 85%, more preferably at least 90%, more preferably at least 95%, most preferably at least 98% homologous to the corresponding nucleotide sequences presented herein over a region of at least 20, preferably at least 25 or 30, for instance at least 40, 60 or 100 or more contiguous nucleotides.

The term "selectively hybridisable" means that the polynucleotide used as a probe is used under conditions where a target polynucleotide of the invention is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10-fold, preferably less than 100-fold as intense as the specific interaction observed with the target DNA. The intensity of interaction may be measured, for example, by radiolabelling the probe, e.g. with $^{32}$P.

In a preferred aspect, the present invention covers nucleotide sequences that can hybridise to any one or more of the nucleotide sequences of the present invention under stringent conditions (e.g. 65° C. and 0.1×SSC {1×SSC=0.15 M NaCl, 0.015 M Na$_3$ Citrate pH 7.0}).

Where the polynucleotide of the present invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other variants of the sequences described herein may be obtained, for example, by probing DNA libraries made from a range of individuals, for example individuals from different populations. In addition, other viral/bacterial, or cellular homologues particularly cellular homologues found in mammalian cells (e.g. bovine, ovine, porcine, equine, rodent and primate cells), may be obtained and such homologues and fragments thereof in general will be capable of selectively hybridising to the sequence shown in SEQ ID NO: 1. Such sequences may be obtained by probing cDNA libraries made from, or genomic DNA libraries derived from, other animal species, and probing such libraries with probes comprising all or part of the sequence shown in SEQ ID NO: 1 under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site-directed mutagenesis of characterised sequences. This may be useful where, for example, silent codon changes are required to sequences to optimise codon preferences for a particular host cell in which the polynucleotide sequences are being expressed. Other sequence changes may, be desired in order to introduce restriction enzyme recognition sites, or to after the property or function of the polypeptides encoded by the polynucleotides.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

REGULATORY SEQUENCES

Preferably, the polynucleotide of the present invention is operably linked to a regulatory sequence which is capable of providing for the expression of the coding sequence, such as by the chosen host cell. By way of example, the present invention covers a vector comprising the polynucleotide of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the polynucleotide encoding the polypeptide of the present invention may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the polypeptide of the present invention.

Preferably, the nucleotide sequence of the present invention may be operably linked to at least a promoter.

Aside from the promoter native to the gene encoding the polypeptide of the present invention, other promoters may be used to direct expression of the polypeptide of the present invention. The promoter may be selected for its efficiency in directing the expression of the polypeptide of the present invention in the desired expression host.

In another embodiment, a constitutive promoter may be selected to direct the expression of the desired polypeptide of the present invention. Such an expression construct may provide additional advantages since it circumvents the need to culture the expression hosts on a medium containing an inducing substrate.

Examples of suitable promoters would be LTR, SV40 and CMV in mammalian systems; E. coli lac or trp in bacterial systems; baculovirus polyhedron promoter (polh) in insect systems and other promoters that are known to control expression in eukaryotic and prokaryotic cells or their viruses.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance or decrease) the levels of expression of the nucleotide sequence of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat, Gene 217 [1987] 217–225; and Dawson, Plant Mol. Biol. 23 [1993] 97).

The expression vector may also contain sequences which act on the promoter to amplify expression. For example, the SV40, CMV, and polyoma cis-acting elements (enhancer) and a selectable marker can provide a phenotypic trait for selection (e.g. dihydrofolate reductase or neomycin resistance for mammalian cells or amplicillin/tetracyclin resistance for E. coli). Selection of the appropriate vector containing the appropriate promoter and selection marker is well within the level of those skilled in the art.

CONSTRUCTS

The term "construct"—which is synonymous with terms such as "conjugate", "cassette" and "hybrid"—includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In each case, the terms do not cover the natural combination of the nucleotide sequence coding for the protein ordinarily associated with the wild-type gene promoter and when they are both in their natural environment.

The construct may even contain or express a marker which allows for the selection of the genetic construct in, for example, mammalian, yeast, insect, fungal or bacterial cells. Various markers exist which may be used, such as, for example, those that provide for antibiotic resistance to G418, hygromycin, bleomycin, kanamycin and gentamycin.

Preferably the construct of the present invention comprises at least the nucleotide sequence of the present invention operably linked to a promoter.

VECTORS

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the same species or may be of a different species. If the construct is capable of being transferred from one species to another—such as from a viral vector such as MMLV or FIV to a human or mammalian primary cell or cell line, then the transformation vector is sometimes referred to as a "shuttle vector".

A large variety of expression systems may be used in different hosts. For example, episomal, chromosomal and virus-derived systems (e.g. vectors derived from bacterial plasmids, bacteriophage, papova virus such as SV40, vaccinia virus, adenovirus, and retrovirus).

The DNA sequence can be inserted into the vector by a variety of techniques. In general the DNA sequence is inserted into an appropriate restriction endonuclease site by procedures known in the art and deemed to be within the scope of those skilled in the art. The DNA sequence in the expression vector is linked operatively to appropriate control sequences that direct mRNA synthesis (i.e the promoter).

The vectors of the present invention may be transformed into a suitable host cell as described below to provide for expression of a polypeptide of the present invention. Thus, in a further aspect, the invention provides a process for preparing polypeptides according to the present invention which comprises cultivating a host cell transformed or transfected with an expression vector as described above under conditions to provide for expression by the vector of a coding sequence encoding the polypeptides, and recovering the expressed polypeptides.

The vectors may be, for example, plasmid, virus or bacteriophage (phage) vectors provided with an origin of replication, optionally a promoter for the expression of the polynucleotide and optionally a regulator of the promoter.

The vectors of the present invention may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in mammalian cells, yeast, but not in filamentous fungi), the ampicillin resistance gene (E. coli), the neomycin resistance gene (mammalian cells) and the E. coli uidA gene, coding for β-glucuronidase (GUS).

Vectors may be used in vitro, for example for the production of RNA or used to transfect or transform a host cell.

Thus, polynucleotides of the present invention can be incorporated into a recombinant vector (typically a replicable vector), for example a cloning or expression vector. The vector may be used to replicate the nucleic acid in a compatible host cell. Thus, in a further embodiment, the invention provides a method of making polynucleotides of the present invention by introducing a polynucleotide of the present invention into a replicable vector, introducing the vector into a compatible host cell, and growing the host cell under conditions which bring about replication of the vector.

The vector may be recovered from the host cell. Suitable host cells are described below in connection with expression vectors.

The present invention also relates to the use of genetically engineered host cells expressing a PFI-002 polypeptide or variant, homologue, fragment, analogue or derivative thereof in screening methods for the identification of modulators (e.g. antagonists or agonists) of PFI-002. Such genetically engineered host cells could be used to screen peptide libraries or organic molecules capable of modulating PFI-002 activity. Modulators (e.g. antagonists) of the PFI-002 polypeptide, such as antibodies, peptides or small organic molecules will provide the basis for pharmaceutical compositions for the treatment of diseases associated with, for example, PFI-002. Such modulators (e.g. antagonists) can be administered alone or in combination with other therapeutics for the treatment of such diseases.

The present invention also relates to expression vectors and host cells comprising polynucleotide sequences encoding PFI-002 or a variant, homologue, fragment, analogue or derivative thereof for the in vivo or in vitro production of PFI-002 protein or to screen for agents that can affect PFI-002 expression or activity.

TISSUE

The term "tissue" as used herein includes tissue per se and organ.

HOST CELLS

The term "host cell"—in relation to the present invention—includes any cell that could comprise the nucleotide sequence coding for the recombinant protein according to the present invention and/or products obtained therefrom, wherein a promoter can allow expression of the nucleotide sequence according to the present invention when present in the host cell.

Thus, a further embodiment of the present invention provides host cells transformed or transfected with a polynucleotide of the present invention. Preferably said polynucleotide is carried in a vector for the replication and expression of said polynucleotide. The cells will be chosen to be compatible with the said vector and may, for example, be prokaryotic (for example, bacterial cells), or eukaryotic (i.e. mammalian, fungal, insect and yeast cells).

Introduction of polynucleotides into host cells can be effected by methods as described in Sambrook, et al., eds. (1989) Molecular Cloning: A Laboratory Manual, Cold Spring Harbor Laboratory Press, New York, N.Y., USA. These methods include, but are not limited to, calcium phosphate transfection, DEAE-dextran-mediated transfection, cationic lipid-mediated transfection, electroporation, transvection, microinjection, transduction, scrape loading, and ballistic introduction.

Examples of representative hosts include, bacterial cells (e.g E. coli, Steptomyces); fungal cells such as yeast cells and Aspergillus; insect cells such as Drosophila S2 and Spodoptera SF9 cells; animal cells such as CHO, COS, HEK, HeLa, and 3T3 cells. The selection of the appropriate host is deemed to be within the scope of those skilled in the art.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly expressed or secreted from the yeast cell, or in some cases are not processed properly (e.g. hyperglycosylation in yeast). In these instances, a different fungal host organism should be selected.

Examples of suitable expression hosts within the scope of the present invention are fungi such as Aspergillus species (such as those described in EP-A-0184438 and EP-A-0284603) and Trichoderma species; bacteria such as Escherichia species, Streptomyces species and Pseudomonas species; and yeasts such as Kluyveromyces species (such as those described in EP-A-0096430 and EP-A-0301670) and Saccharomyces species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Kluyveromyces lactis, Schizosaccharomyces pombe, Pichia pastoris* and *Saccharomyces cerevisiae.*

The use of suitable host cells—such as mammalian, yeast, insect and fungal host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

ORGANISM

The term "organism" in relation to the present invention includes any organism, except man, that could comprise the nucleotide sequence coding for the recombinant protein according to the present invention and/or products obtained therefrom, wherein a promoter can allow expression of the nucleotide sequence according to the present invention when present in the organism. Examples of organisms may include a fungus, yeast or protozoan.

The term "transgenic organism" in relation to the present invention includes any organism, except man, that comprises the nucleotide sequence coding for the protein according to the present invention and/or products obtained therefrom, wherein the promoter can allow expression of the nucleotide sequence according to the present invention within the organism. Preferably the nucleotide sequence is incorporated in the genome of the organism.

The term "transgenic organism" does not cover the native nucleotide coding sequence according to the present invention in its natural environment when it is under the control of its native promoter which is also in its natural environment in addition, the present invention does not cover the native protein according to the present invention when it is in its natural environment and when it has been expressed by its native nucleotide coding sequence which is also in its natural environment and when that nucleotide sequence is under the control of its native promoter which is also in its natural environment.

Therefore, the transgenic organism of the present invention includes an organism comprising any one of, or combinations of, the nucleotide sequence coding for the amino acid sequence according to the present invention, constructs according to the present invention (including combinations thereof), vectors according to the present invention, plasmids according to the present invention, cells according to the present invention, and tissues according to the present invention or the products thereof. The transformed cell or organism could prepare acceptable quantities of the desired compound which would be easily retrievable from the cell or organism.

TRANSFORMATION OF HOST CELLS/HOST ORGANISMS

As indicated earlier, the host organism can be a prokaryotic or a eukaryotic organism. An example of a suitable prokaryotic host is *E. coli*. Teachings on the transformation of prokaryotic hosts are well documented in the art, for example see Sambrook et al. (Molecular Cloning: A Laboratory Manual, 2nd edition, 1989, Cold Spring Harbor Laboratory Press, New York, N.Y., USA) and Ausubel et al. (Current Protocols in Molecular Biology (1995), John Wiley & Sons, Inc.).

In a preferred embodiment, the transformed host is a mammalian cell or, for example, an insect cell, wherein introduction of polynucleotides into said host cells can be effected by methods as described in, for example, Sambrook et al. (Molecular Cloning: A Laboratory Manual, 2nd edition, 1989, Cold Spring Harbor Laboratory. Press, New York, N.Y., USA). These methods include, but are not limited to, calcium phosphate transfection, DEAE-dextran-mediated transfection, cationic lipid-mediated transfection, electroporation, transvection, microinjection, transduction, scrape loading, and ballistic introduction.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al. (1987, Yeast Biotechnology, D R Berry et al, eds, pp 401–429, Allen and Unwin, London) and by King et al. (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae.*

A review of the principles of heterologous gene expression in *Saccharomyces cerevisiae* and secretion of gene products is given by E Hinchcliffe and E Kenny ("Yeast as a vehicle for the expression of heterologous genes", 1993, Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al. (1978, Proceedings of the National Academy of Sciences of the USA, 75: 1929); Beggs, J D (1978, Nature, London, 275:104); and Ito, H et al. (1983, J. Bacteriology 153:163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Thus, the present invention also provides a method of transforming a host cell with a nucleotide sequence shown in SEQ ID NO: 1 or a derivative, homologue, variant, analogue or fragment thereof.

Host cells transformed with a PFI-002 nucleotide coding sequence may be cultured under conditions suitable for the expression and recovery of the encoded protein (in cell membranes) from cell culture. The protein produced by a recombinant cell may be expressed on the cell surface, secreted or may be contained intracellularly depending on the sequence and/or the vector used. As will be understood by those of skill in the art, expression vectors containing PFI-002 coding sequences will generally enable expression in the cell membrane. Other recombinant constructions may join PFI-002 coding sequence to nucleotide sequence encoding a polypeptide domain which will facilitate protein purification/identification (Kroll D J et al. (1993) DNA Cell Biol Vol 12 p441–53, see also above discussion of vectors containing fusion proteins).

GENETICALLY ENGINEERED or GENETICALLY MODIFIED

A cell, preferably an animal cell, that is "genetically modified" is heterozygous or homozygous for a modification that is introduced into the cell, or into a progenitor cell, by genetic engineering. The standard methods of genetic engineering that are available for introducing the modification include homologous recombination, viral vector gene trapping, irradiation, chemical mutagenesis, and the transgenic expression of a nucleotide sequence encoding antisense RNA alone or in combination with catalytic ribozymes. Preferred methods for genetic modification are homologous recombination and viral vector gene trapping which both modify an endogenous gene by inserting a foreign nucleic acid sequence into the gene locus. A nucleic acid sequence that is foreign to the gene is an exogenous sequence that is non-naturally occurring in the gene. This insertion of foreign DNA can occur within any region of the PFI-002 gene, e.g., in an enhancer, promoter, regulator region, non-coding region, coding region, intron, or exon. The most preferred method of genetic engineering is homologous recombination, in which the foreign nucleic acid sequence is inserted in a targeted manner either alone or in combination with a deletion of a portion of the endogenous gene sequence.

FUNCTIONALLY DISRUPTED

By a PFI-002 gene that is "functionally disrupted" is meant a PFI-002 gene that is genetically modified such that the cellular activity of the PFI-002 polypeptide encoded by the disrupted gene is decreased in cells that normally express the wild-type version of the PFI-002 gene. When the genetic modification effectively eliminates all wild-type copies of the PFI-002 gene in a cell (e.g., the genetically modified cell, preferably an animal cell, is homozygous for the PFI-002 gene disruption or the only wild-type copy of PFI-002 gene originally present is now disrupted), then the genetic modification results in a reduction in PFI-002 polypeptide activity (i.e. reduced receptor expression) as compared to an appropriate control cell that expresses the wild-type PFI-002 gene. This reduction in PFI-002 polypeptide activity (i.e. reduced receptor expression) results from either reduced PFI-002 gene expression (i.e., PFI-002 mRNA levels are effectively reduced and produce reduced levels of PFI-002 polypeptide) and/or because the disrupted PFI-002 gene encodes a mutated polypeptide with reduced function or stability as compared to a wild-type PFI-002 polypeptide. Preferably, the activity (i.e. reduced receptor expression) of PFI-002 polypeptide in the genetically modified cell is reduced to 50% or less of wild-type levels, more preferably, to 25% or less, and, even more preferably, to 10% or less of wild-type levels. Most preferably, the PFI-002 gene disruption results in a null mutation.

GENETICALLY MODIFIED ANIMAL CELL

By a "genetically modified animal cell" containing a functionally disrupted PFI-02 gene is meant an animal cell, including a human cell, created by genetic engineering to contain a functionally disrupted PFI-002 gene, as well as daughter cells that inherit the disrupted PFI-002 gene. These cells may be genetically modified in culture according to any standard method known in the art. As an alternative to genetically modifying the cells in culture, non-human mammalian cells may also be isolated from a genetically modified, non-human mammal that contains a PFI-002 gene disruption. The animal cells of the invention may be obtained from primary cell or tissue preparations as well as culture-adapted, tumorigenic, or transformed cell lines. These cells and cell lines are derived, for example, from endothelial cells, epithelial cells, islets, neurons and other neural tissue-derived cells, mesothelial cells, osteocytes, lymphocytes, chondrocytes, hematopoietic cells, immune cells, cells of the major glands or organs (e.g., liver, lung, heart, stomach, pancreas, kidney, and skin), muscle cells (including cells from skeletal muscle, smooth muscle, and cardiac muscle), exocrine or endocrine cells, fibroblasts, and embryonic and other totipotent or pluripotent stem cells (e.g., embryonic stem (ES) cells, ES-like cells, and embryonic germline (EG) cells, and other stem cells, such as progenitor cells and tissue-derived stem cells). The preferred genetically modified cells are ES cells, more preferably, mouse or rat ES cells, and, most preferably, human ES cells.

A "homology region" used in a targeting vector for homologous recombination with a PFI-002 gene is related (i.e., complementary) to a portion of the PFI-002 gene or a sequence flanking the PFI-002 gene to a degree sufficient to allow hybridization to occur between the homology region and the PFI-002 gene sequence under standard low stringency conditions known in the art (e.g., as described in Current Protocols in Human Genetics, unit 4.1, John Wiley & Sons, New York, N.Y., 2000).

By an "ES cell" or an "ES-like cell" is meant a pluripotent stem cell derived from an embryo, from a primordial germ cell, or from a teratocarcinoma, that is capable of indefinite self renewal as well as differentiation into cell types that are representative of all three embryonic germ layers.

By "reduced" is meant a statistically significant decrease (i.e., $p<0.1$).

The genetically modified animal cells, including human cells, of the invention are heterozygous or homozygous for a modification that functionally disrupts the PFI-002 gene.

The animal cells may be derived by genetically engineering cells in culture, or, in the case of non-human mammalian cells, the cells may be isolated from genetically modified, non-human mammals.

The PFI-002 gene locus is functionally disrupted by one of the several techniques for genetic modification known in the art, including chemical mutagenesis (Rinchik, Trends in Genetics 7: 15–21, 1991, Russell, Environmental & Molecular Mutagenesis 23 (Suppl. 24) 23–29 1994), irradiation (Russell, supra), transgenic expression of PFI-002 gene antisense RNA, either alone or in combination with a catalytic RNA ribozyme sequence (Luyckx et al., Proc. Natl. Acad. Sci. 96:12174–79, 1999; Sokol et al., Transgenic Research 5: 363–71, 1996; Efrat et al., Proc. Natl. Acad. Sci. USA 91: 2051–55, 1994; Larsson et al., Nucleic Acids Research 22: 2242–48, 1994) and, as further discussed below, the disruption of the PFI-002 gene by the insertion of a foreign nucleic acid sequence into the PFI-002 gene locus. Preferably, the foreign sequence is inserted by homologous recombination or by the insertion of a viral vector. Most preferably, the method of PFI-002 gene disruption is homologous recombination and includes a deletion of a portion of the endogenous PFI-002 gene sequence.

The integration of the foreign sequence functionally disrupts the PFI-002 gene through one or more of the following mechanisms: by interfering with the PFI-002 gene transcription or translation process (e.g., by interfering with promoter recognition, or by introducing a transcription termination site or a translational stop codon into the PFI-002 gene); or by distorting the PFI-002 gene coding sequence such that it no longer encodes a PFI-002 polypeptide with normal receptor function (e.g., by inserting a foreign coding sequence into the PFI-002 gene coding sequence, by introducing a frameshift mutation or amino acid(s) substitution, or, in the case of a double crossover event, by deleting a portion of the PFI-002 gene coding sequence that is required for expression of a functional receptor protein).

To insert a foreign sequence into a PFI-002 gene locus in the genome of a cell, the foreign DNA sequence is introduced into the cell according to a standard method known in the art such as electroporation, calcium-phosphate precipitation, retroviral infection, microinjection, biolistics, liposome transfection, DEAE-dextran transfection, or transferrinfection (see, e.g., Neumann et al., EMBO J. 1: 841–845, 1982; Potter et al., Proc. Natl. Acad. Sci USA 81: 7161–65, 1984; Chu et al., Nucleic Acids Res. 15: 1311–26, 1987; Thomas and Capecchi, Cell 51: 503–12, 1987; Baum et al., Biotechniques 17: 1058–62, 1994; Biewenga et al., J. Neuroscience Methods 71: 67–75, 1997; Zhang et al., Biotechniques 15: 868–72, 1993; Ray and Gage, Biotechniques 13: 598–603, 1992; Lo, Mol. Cell. Biol. 3: 1803–14, 1983; Nickoloff et al., Mol. Biotech. 10: 93–101, 1998; Linney et al., Dev. Biol. (Orlando) 213: 207–16, 1999; Zimmer and Gruss, Nature 338: 150–153, 1989; and Robertson et al., Nature 323: 445–48, 1986). The preferred method for introducing foreign DNA into a cell is electroporation.

Homologous Recombination

The method of homologous recombination targets the PFI-002 gene for disruption by introducing a PFI-002 gene targeting vector into a cell containing a PFI-002 gene. The ability of the vector to target the PFI-002 gene for disruption stems from using a nucleotide sequence in the vector that is homologous to the PFI-002 gene. This homology region facilitates hybridization between the vector and the endogenous sequence of the PFI-002 gene. Upon hybridization, the probability of a crossover event between the targeting vector and genomic sequences greatly increases. This crossover event results in the integration of the vector sequence into the PFI-002 gene locus and the functional disruption of the PFI-002 gene.

General principles regarding the construction of vectors used for targeting are reviewed in Bradley et al. (Biotechnol. 10: 534, 1992). Two different exemplary types of vector can be used to insert DNA by homologous recombination: an insertion vector or a replacement vector. An insertion vector is circular DNA which contains a region of PFI-002 gene homology with a double stranded break. Following hybridization between the homology region and the endogenous PFI-002 gene, a single crossover event at the double stranded break results in the insertion of the entire vector sequence into the endogenous gene at the site of crossover.

The more preferred vector to use for homologous recombination is a replacement vector, which is colinear rather than circular. Replacement vector integration into the PFI-002 gene requires a double crossover event, i.e. crossing over at two sites of hybridization between the targeting vector and the PFI-002 gene. This double crossover event results in the integration of vector sequence that is sandwiched between the two sites of crossover into the PFI-002 gene and the deletion of the corresponding endogenous PFI-002 gene sequence-that originally spanned between the two sites of crossover (see, e.g., Thomas and Capecchi et al., Cell 51: 503–12, 1987; Mansour et al., Nature 336: 348–52, 1988; Mansour et al., Proc. Natl. Acad. Sci. USA 87: 7688–7692, 1990; and Mansour, GATA 7: 219–227, 1990).

A region of homology in a targeting vector is generally at least 100 nucleotides in length. Most preferably, the homology region is at least 1–5 kilobases (Kb) in length. Although there is no demonstrated minimum length or minimum degree of relatedness required for a homology region, targeting efficiency for homologous recombination generally corresponds with the length and the degree of relatedness between the targeting vector and the PFI-002 gene locus. In the case where a replacement vector is used, and a portion of the endogenous PFI-002 gene is deleted upon homologous recombination, an additional consideration is the size of the deleted portion of the endogenous PFI-002 gene. If this portion of the endogenous PFI-002 gene is greater than 1 Kb in length, then a targeting cassette with regions of homology that are longer than 1 Kb is recommended to enhance the efficiency of recombination. Further guidance regarding the selection and use of sequences effective for homologous recombination is described in the literature (see, e.g., Deng and Capecchi, Mol. Cell. Biol. 12: 3365–3371, 1992; Bollag et al., Annu. Rev. Genet. 23: 199–225, 1989; and Waldman and Liskay, Mol. Cell. Biol. 8: 5350–5357, 1988).

A wide variety of cloning vectors may be used as vector backbones in the construction of PFI-002 gene targeting vectors, including pBluescript-related plasmids (e.g., Bluescript KS+11), pQE70, pQE60, pQE-9, pBS, pD10, phagescript, phiPFI-002174, pBK Phagemid, pNH8A, pNH16a, pNH18Z, pNH46A, ptrc99a, pKK223-3, pKK233-3, pDR540, and pRIT5 PWLNEO, pSV2CAT, pPFI-002T1, pSG (Stratagene), pSVK3, PBPV, PMSG, and pSVL, pBR322 and pBR322-based vectors, pBM9, pBR325, pKH47, pBR328, pHC79, phage Charon 28, pKB11, pKSV-10, pK19 related plasmids, pUC plasmids, and the pGEM series of plasmids. These vectors are available from a variety of commercial sources (e.g., Boehringer Mannheim Biochemicals, Indianapolis, Ind.; Qiagen, Valencia, Calif.; Stratagene, La Jolla, Calif.; Promega, Madison, Wis.; and New England Biolabs, Beverly, Mass.). However, any other vectors, e.g. plasmids, viruses, or parts thereof, may be used as long as they are replicable and viable in the desired host. The vector may also comprise sequences which enable it to replicate in the host whose genome is to be modified. The use of such a vector can expand the interaction period during which recombination can occur, increasing the efficiency of targeting (see Molecular Biology, ed. Ausubel et al, Unit 9.16, FIG. 9.16.1).

The specific host employed for propagating the targeting vectors described above is not critical. Examples include *E. coli* K12 RR1 (Bolivar et al., Gene 2: 95, 1977), *E. coli* K12 HB101 (ATCC No. 33694), *E. coli* MM21 (ATCC No. 336780), *E. coli* DH1 (ATCC No. 33849), *E. coli* strain DH5α, and *E. coli* STBL2. Alternatively, hosts such as *C. cerevisiae* can be used. The above-mentioned hosts are available commercially (e.g., Stratagene, La Jolla, Calif.; and Life Technologies, Rockville, Md.).

To create the targeting vector, a PFI-002 gene targeting construct is added to an above-described vector backbone. The PFI-002 gene targeting constructs described above have at least one PFI-002 gene homology region. To make the PFI-002 gene homology regions, a PFI-002 gene-related sequence is used as a basis for producing polymerase chain reaction (PCR) primers. These primers are used to amplify the desired region of the PFI-002 sequence by high fidelity PCR amplification (Mattila et al., Nucleic Acids Res. 19: 4967, 1991; Eckert and Kunkel 1: 17, 1991; and U.S. Pat. No. 4,683,202). The genomic sequence is obtained from a genomic clone library or from a preparation of genomic DNA, preferably from the animal species that is to be targeted for PFI-002 gene disruption.

Preferably, the targeting constructs described above also include an exogenous nucleotide sequence encoding a positive marker protein. The stable expression of a positive marker after vector integration confers an identifiable characteristic on the cell without compromising cell viability. Therefore, in the case of a replacement vector, the marker gene is positioned between two flanking homology regions so that it integrates into the PFI-002 gene following the double crossover event.

It is preferred that the positive marker protein is a selectable protein; the stable expression of such a protein in a cell confers a selectable phenotypic characteristic, i.e., the characteristic enhances the survival of the cell under otherwise lethal conditions. Thus, by imposing the selectable condition, one can isolate cells that stably express the positive selectable marker from other cells that have not successfully integrated the vector sequence on the basis of viability. Examples of positive selectable marker proteins (and their agents of selection) include Neo (G418 or kanomycin), Hyg (hygromycin), HisD (histidinol), Gpt (xanthine), Ble (bleomycin), and Hprt (hypoxanthine) (see, e.g., Capecchi and Thomas, U.S. Pat. No. 5,464,764, and Capecchi, Science 244: 1288–92, 1989). Other positive markers that may also be used as an alternative to a selectable marker include reporter proteins such as β-galactosidase, firefly luciferase, or green fluorescent protein (see, e.g., Current Protocols in Cytometry, Unit 9.5, and Current Protocols in Molecular Biology, Unit 9.6, John Wiley & Sons, New York, N.Y., 2000).

The above-described positive selection scheme does not distinguish between cells that have integrated the vector by targeted homologous recombination at the PFI-002 gene locus versus random, non-homologous integration of vector sequence into any chromosomal position. Therefore, when using a replacement vector for homologous recombination, it is also preferred to include a nucleotide sequence encoding a negative selectable marker protein. Expression of a negative selectable marker causes a cell expressing the marker to lose viability when exposed to a certain agent (i.e., the marker protein becomes lethal to the cell under certain selectable conditions). Examples of negative selectable markers (and their agents of lethality) include herpes simplex virus thymidine kinase (gancyclovir or 1,2-deoxy-2-fluoro-α-d-arabinofuransyl-5-iodourecil), Hprt (6-thioguanine or 6-thioxanthine), and diphtheria toxin, ricin toxin, and cytosine deaminase (5-fluorocytosine).

The nucleotide sequence encoding the negative selectable marker is positioned outside of the two homology regions of the replacement vector. Given this positioning, cells will only integrate and stably express the negative selectable marker if integration occurs by random, non-homologous recombination; homologous recombination between the PFI-002 gene and the two regions of homology in the targeting construct excludes the sequence encoding the negative selectable marker from integration. Thus, by imposing the negative condition, cells that have integrated the targeting vector by random, non-homologous recombination lose viability.

The above-described combination of positive and negative selectable markers is preferred because a series of positive and negative selection steps can be designed to more efficiently select only those cells that have undergone vector integration by homologous recombination, and, therefore, have a potentially disrupted PFI-002 gene. Further examples of positive-negative selection schemes, selectable markers, and targeting constructs are described, for example, in U.S. Pat No. 5,464,764, WO 94/06908, and Valancius and Smithies, Mol. Cell. Biol. 11: 1402, 1991.

In order for a marker protein to be stably expressed upon vector integration, the targeting vector may be designed so that the marker coding sequence is operably linked to the endogenous PFI-002 gene promoter upon vector integration. Expression of the marker is then driven by the PFI-002 gene promoter in cells that normally express PFI-002 gene. Alternatively, each marker in the targeting construct of the vector may contain its own promoter that drives expression independent of the PFI-002 gene promoter. This latter scheme has the advantage of allowing for expression of markers in cells that do not typically express the PFI-002 gene (Smith and Berg, Cold Spring Harbor Symp. Quant. Biol. 49: 171, 1984; Sedivy and Sharp, Proc. Natl. Acad. Sci. (USA) 86: 227: 1989; Thomas and Capecchi, Cell 51: 503, 1987).

Exogenous promoters that can be used to drive marker gene expression include cell-specific or stage-specific promoters, constitutive promoters, and inducible or regulatable promoters. Non-limiting examples of these promoters include the herpes simplex thymidine kinase promoter, cytomegalovirus (CMV) promoter/enhancer, SV40 promoters, PGK promoter, PMC1-neo, metallothionein promoter, adenovirus late promoter, vaccinia virus 7.5K promoter, avian beta globin promoter, histone promoters (e.g., mouse histone H3-614), beta actin promoter, neuron-specific enolase, muscle actin promoter, and the cauliflower mosaic virus 35S promoter (see generally, Sambrook et al., *Molecular Cloning*, Vols. I–III, Cold Spring Harbor Laboratory Press, Cold Spring Harbor, N.Y., 1989, and *Current Protocols in Molecular Biology*, John Wiley & Sons, New York, N.Y., 2000; Stratagene, La Jolla, Calif.).

To confirm whether cells have integrated the vector sequence into the targeted PFI-002 gene locus, primers or genomic probes that are specific for the desired vector integration event can be used in combination with PCR or Southern blot analysis to identify the presence of the desired vector integration into the PFI-002 gene locus (Erlich et al., Science 252: 1643–51, 1991; Zimmer and Gruss, Nature 338: 150, 1989; Mouellic et al., Proc. Natl. Acad. Sci. (USA) 87: 4712, 1990; and Shesely et al., Proc. Natl. Acad. Sci. (USA) 88: 4294, 1991).

Gene Trapping

Another method available for inserting a foreign nucleic acid sequence into the PFI-002 gene locus to functionally disrupt the PFI-002 gene is gene trapping. This method takes advantage of the cellular machinery present in all mammalian cells that splices exons into mRNA to insert a gene trap vector coding sequence into a gene in a random fashion. Once inserted, the gene trap vector creates a mutation that may functionally disrupt the trapped PFI-002 gene. In contrast to homologous recombination, this system for mutagenesis creates largely, random mutations. Thus, to obtain a genetically modified cell that contains a functionally disrupted PFI-002 gene, cells containing this particular mutation must be identified and selected from a pool of cells that contain random mutations in a variety of genes.

Gene trapping systems and vectors have been described for use in genetically modifying murine cells and other cell types (see, e.g., Allen et al., Nature 333: 852–55, 1988; Bellen et al., Genes Dev. 3: 1288–1300, 1989; Bier et al., Genes Dev. 3: 1273–1287, 1989; Bonnerot et al., J. Virol. 66: 4982–91, 1992; Brenner et al., Proc. Nat. Acad. Sci. USA 86: 5517–21, 1989; Chang et al., Virology 193: 737–47, 1993; Friedrich and Soriano, Methods Enzymol. 225: 681–701, 1993; Friedrich and Soriano, Genes Dev. 5: 1513–23, 1991; Goff, Methods Enzymol. 152: 469–81, 1987; Gossler et al., Science 244: 463–65, 1989; Hope, Develop. 113: 399–408, 1991; Kerr et al., Cold Spring Harb. Symp. Quant. Biol. 2: 767–776, 1989; Reddy et al., J. Virol. 65: 1507–1515, 1991; Reddy et al., Proc. Natl. Acad. Sci. U.S.A. 89: 6721–25, 1992; Skarnes et al., Genes Dev. 6: 903–918, 1992; von Melchner and Ruley, J. Virol. 63: 3227–3233, 1989; and Yoshida et al., Transgen. Res. 4: 277–87, 1995).

Promoter trap (5' trap) vectors contain, in 5' to 3' order, a splice acceptor sequence followed by an exon, which is typically characterized by a translation initiation codon and open reading frame (ORF) and/or an internal ribosome entry site. In general, these promoter trap vectors do not contain promoters or operably linked splice donor sequences. Consequently, after integration into the cellular genome of the host cell, the promoter trap vector sequence intercepts the normal splicing of the upstream gene and acts as a terminal exon. Expression of the vector coding sequence is dependent upon the vector integrating into an intron of the disrupted gene in the proper reading frame. In such a case, the cellular splicing machinery splices exons from the trapped gene upstream of the vector coding sequence (Zambrowicz et al., WO 99/50426).

An alternative method for producing an effect similar to the above-described promoter trap vector is a vector that incorporates a nested set of stop codons present in, or otherwise engineered into, the region between the splice acceptor of the promoter trap vector and the translation initiation codon or polyadenylation sequence. The coding sequence can also be engineered to contain an independent ribosome entry site (IRES) so that the coding sequence will be expressed in a manner largely independent of the site of integration within the host cell genome. Typically, but not necessarily, an IRES is used in conjunction with a nested set of stop codons.

Another type of gene trapping scheme uses a 3' gene trap vector. This type of vector contains, in operative combination, a promoter region, which mediates expression of an adjoining coding sequence, the coding sequence, and a splice donor sequence that defines the 3' end of the coding sequence exon. After integration into a host cell genome, the transcript expressed by the vector promoter is spliced to a splice acceptor sequence from the trapped gene that is located downstream of the integrated gene trap vector sequence. Thus, the integration of the vector results in the expression of a fusion transcript comprising the coding sequence of the 3' gene trap cassette and any downstream cellular exons, including the terminal exon and its polyadenylation signal. When such vectors integrate into a gene, the cellular splicing machinery splices the vector coding sequence upstream of the 3' exons of the trapped gene. One advantage of such vectors is that the expression of the 3' gene trap vectors is driven by a promoter within the gene trap cassette and does not require integration into a gene that is normally expressed in the host cell (Zambrowicz et al., WO 99/50426). Examples of transcriptional promoters and enhancers that may be incorporated into the 3' gene trap vector include those discussed above with respect to targeting vectors.

The viral vector backbone used as the structural component for the promoter or 3' gene trap vector may be selected from a wide range of vectors that can be inserted into the genome of a target cell. Suitable backbone vectors include, but are not limited to, herpes simplex virus vectors, adenovirus vectors, adeno-associated virus vectors, retroviral vectors, lentiviral vectors, pseudorabies virus, alpha-herpes virus vectors, and the like. A thorough review of viral vectors, in particular, viral vectors suitable for modifying non-replicating cells and how to use such vectors in conjunction with the expression of an exogenous polynucleotide sequence, can be found in *Viral Vectors: Gene Therapy and Neuroscience Applications*, Eds. Caplitt and Loewy, Academic Press, San Diego, 1995.

Preferably, retroviral vectors are used for gene trapping. These vectors can be used in conjunction with retroviral packaging cell lines such as those described in U.S. Pat. No. 5,449,614. Where non-murine mammalian cells are used as target cells for genetic modification, amphotropic or pantropic packaging cell lines can be used to package suitable vectors (Ory et al., Proc. Natl. Acad. Sci., USA 93: 11400–11406, 1996). Representative retroviral vectors that can be adapted to create the presently described 3' gene trap vectors are described, for example, in U.S. Pat. No. 5,521,076.

The gene trapping vectors may contain one or more of the positive marker genes discussed above with respect to targeting vectors used for homologous recombination. Similar to their use in targeting vectors, these positive markers are used in gene trapping vectors to identify and select cells that have integrated the vector into the cell genome. The marker gene may be engineered to contain an independent ribosome entry site (IRES) so that the marker will be expressed in a manner largely independent of the location in which the vector has integrated into the target cell genome.

Given that gene trap vectors will integrate into the genome of infected host cells in a fairly random manner, a genetically modified cell having a disrupted PFI-002 gene must be identified from a population of cells that have undergone random vector integration. Preferably, the genetic modifications in the population of cells are of sufficient randomness and frequency such that the population represents mutations in essentially every gene found in the cell's genome, making it likely that a cell with a disrupted PFI-002 gene will be identified from the population (see Zambrowicz et al., WO 99/50426; Sands et al., WO 98/14614).

Individual mutant cell lines containing a disrupted PFI-002 gene are identified in a population of mutated cells using, for example, reverse transcription and PCR (RT-PCR) to identify a mutation in a PFI-002 gene sequence. This process can be streamlined by pooling clones. For example, to find an individual clone containing a disrupted PFI-002 gene, RT-PCR is performed using one primer anchored in the gene trap vector and the other primer located in the PFI-002 gene sequence. A positive RT-PCR result indicates that the vector sequence is encoded in the PFI-002 gene transcript, indicating that PFI-002 gene has been disrupted by a gene trap integration event (see, e.g., Sands et al., WO 98/14614).

Temporal, Spatial, and Inducible Gene Disruptions

A functional disruption of the endogenous PFI-002 gene can occur at specific developmental or cell cycle stages (temporal disruption) or in specific cell types (spatial disruption). The PFI-002 gene disruption can also be inducible when certain conditions are present. A recombinase excision system, such as a Cre-Lox system, may be used to activate or inactivate the PFI-002 gene at a specific developmental stage, in a particular tissue or cell type, or under particular environmental conditions. Generally, methods utilizing Cre-Lox technology are carried out as described by Torres and Kuhn, *Laboratory Protocols for Conditional Gene Targeting*, Oxford University Press, 1997. Methodology similar to that described for the Cre-Lox system can also be employed utilizing the FLP-FRT system. Further guidance regarding the use of recombinase excision systems for conditionally disrupting genes by homologous recombination or viral insertion is provided, for example, in U.S. Pat. No. 5,626,159, U.S. Pat. No. 5,527,695, U.S. Pat. No. 5,434,066, WO 98/29533, Orban et al., Proc. Nat. Acad. Sci. USA 89: 6861–65, 1992; O'Gorman et al., Science 251: 1351–55, 1991; Sauer et al., Nucleic Acids Research 17: 147–61, 1989; Barinaga, Science 265: 26–28, 1994; and Akagi et al., Nucleic Acids Res. 25: 1766–73, 1997. More than one recombinase system can be used to genetically modify an animal cell.

When using homologous recombination to disrupt the PFI-002 gene in a temporal, spatial, or inducible fashion, using a recombinase system such as the Cre-Lox system, a portion of the PFI-002 gene coding region is replaced by a targeting construct comprising the PFI-002 gene coding region flanked by loxP sites. Animal cells carrying this genetic modification contain a functional, loxP-flanked PFI-002 gene. The temporal, spatial, or inducible aspect of the PFI-002 gene disruption is caused by the expression pattern of an additional transgene, a Cre recombinase transgene, that is expressed in the animal cell under the control of the desired spatially-regulated, temporally-regulated, or inducible promoter, respectively. A Cre recombinase targets the loxP sites for recombination. Therefore, when Cre expression is activated, the LoxP sites undergo recombination to excise the sandwiched PFI-002 gene coding sequence, resulting in a functional disruption of the PFI-002 gene (Rajewski et al., J. Clin. Invest. 98: 600–03, 1996; St.-Onge et al., Nucleic Acids Res. 24: 3875–77, 1996; Agah et al., J. Clin. Invest. 100: 169–79, 1997; Brocard et al., Proc. Natl. Acad. Sci. USA 94: 14559–63, 1997; Feil et al., Proc. Natl. Acad. Sci. USA 93: 10887–90, 1996; and Kühn et al., Science 269: 1427–29, 1995).

A cell containing both a Cre recombinase transgene and loxP-flanked PFI-002 gene can be generated through standard transgenic techniques. Further guidance regarding the use of recombinase systems specific promoters to temporally, spatially, or conditionally disrupt the PFI-002 gene is found, for example, in Sauer, Meth. Enz. 225: 890–900, 1993, Gu et al., Science 265: 103–06, 1994, Araki et al., J. Biochem. 122: 977–82, 1997, Dymecki, Proc. Natl. Acad. Sci. 93: 6191–96, 1996, and Meyers et al., Nature Genetics 18: 136–41, 1998.

An inducible disruption of the PFI-002 gene can also be achieved, by using a tetracycline responsive binary system (Gossen and Bujard, Proc. Natl. Acad. Sci. USA 89: 5547–51, 1992). This system involves genetically modifying a cell to introduce a Tet promoter into the endogenous PFI-002 gene regulatory element and a transgene expressing a tetracycline-controllable repressor (TetR). In such a cell, the administration of tetracycline activates the TetR which, in turn, inhibits PFI-002 gene expression and, therefore, functionally disrupts the PFI-002 gene (St.-Onge et al., Nucleic Acids Res. 24: 3875–77, 1996, U.S. Pat. No. 5,922,927).

The above-described systems for temporal, spatial, and inducible disruptions of the PFI-002 gene can also be adopted when using gene trapping as the method of genetic modification, for example, as described, for example, in WO 98/29533.

Creating Genetically Modified Animal Cells

The above-described methods for genetic modification can be used to functionally disrupt a PFI-002 gene in virtually any type of somatic or stem cell derived from an animal. Genetically modified animal cells of the invention include, but are not limited to, mammalian cells, including human cells, and avian cells. These cells may be derived from genetically engineering any animal cell line, such as culture-adapted, tumorigenic, or transformed cell lines, or they may be isolated from a genetically modified, non-human mammal carrying the desired PFI-002 genetic modification.

The cells may be heterozygous or homozygous for the disrupted PFI-002 gene. To obtain cells that are homozygous for the PFI-002 gene disruption (PFI-002–/–), direct, sequential targeting of both alleles can be performed. This process can be facilitated by recycling a positive selectable marker. According to this scheme the nucleotide sequence encoding the positive selectable marker is removed following the disruption of one allele using the Cre-Lox P system. Thus, the same vector can be used in a subsequent round of targeting to disrupt the second PFI-002 gene allele (Abuin and Bradley, Mol. Cell. Biol. 16: 1851–56, 1996; Sedivy et al., T.I.G. 15: 88–90, 1999; Cruz et al., Proc. Natl. Acad. Sci. (USA) 88: 7170–74, 1991; Mortensen et al., Proc. Natl. Acad. Sci. (USA) 88: 7036–40, 1991; te Riele et al., Nature (London) 348: 649–651, 1990).

An alternative strategy for obtaining ES cells that are PFI-002–/– is the homogenotization of cells from a population of cells that is heterozygous for the PFI-002 gene disruption (PFI-002+/–). The method uses a scheme in which PFI-002+/– targeted clones that express a selectable drug resistance marker are selected against a very high drug concentration; this selection favours cells that express two copies of the sequence encoding the drug resistance marker and are, therefore, homozygous for the PFI-002 gene disruption (Mortensen et al., Mol. Cell. Biol. 12: 2391–95, 1992).

Following the genetic modification of the desired cell or cell line, the PFI-002 gene locus can be confirmed as the site of modification by PCR analysis according to standard PCR or Southern blotting methods known in the art (see, e.g., U.S. Pat. No. 4,683,202; and Erlich et al., Science 252: 1643, 1991). Further verification of the functional disruption of the PFI-002 gene may also be made if PFI-002 gene messenger RNA (mRNA) levels and/or PFI-002 polypeptide levels are reduced in cells that normally express the PFI-002 gene. Measures of PFI-002 gene mRNA levels may be obtained by using reverse transcriptase mediated polymerase chain reaction (RT-PCR), Northern blot analysis, or in situ hybridization. The quantification of PFI-002 polypeptide levels produced by the cells can be made, for example, by standard immunoassay methods known in the art. Such immunoassays include but are not limited to, competitive and non-competitive assay systems using techniques such as radioimmunoassays, ELISA (enzyme-linked immunosorbent assay), "sandwich" immunoassays, immunoradiometric assays, gel diffusion precipitin reactions, immunodiffusion assays, in situ immunoassays (using colloidal gold, enzymatic, or radioisotope labels, for example), Western blots, 2-dimensional gel analysis, precipitation reactions, immunofluorescence assays, protein A assays, and immunoelectrophoresis assays.

Preferred genetically modified animal cells are embryonic stem (ES) cells and ES-like cells. These cells are derived from the preimplantation embryos and blastocysts of various species, such as mice (Evans et al., Nature 129:154–156, 1981; Martin, Proc. Natl. Acad. Sci., USA, 78: 7634–7638, 1981), pigs and sheep (Notanianni et al., J. Reprod. Fert. Suppl., 43: 255–260, 1991; Campbell et al., Nature 380: 64–68, 1996) and primates, including humans (Thomson et al., U.S. Pat. No. 5,843,780, Thomson et al., Science 282: 1145–1147, 1995; and Thomson et al., Proc. Natl. Acad. Sci. USA 92: 7844–7848, 1995).

These types of cells are pluripotent. That is, under proper conditions, they differentiate into a wide variety of cell types derived from all three embryonic germ layers: ectoderm, mesoderm and endoderm. Depending upon the culture conditions, a sample of ES cells can be cultured indefinitely as stem cells, allowed to differentiate into a wide variety of different cell types within a single sample, or directed to differentiate into a specific cell type, such as macrophage-like cells, neuronal cells, cardiomyocytes, adipocytes, smooth muscle cells, endothelial cells, skeletal muscle cells, keratinocytes, and hematopoietic cells, such as eosinophils, mast cells, erythroid progenitor cells, or megakaryocytes. Directed differentiation is accomplished by including specific growth factors or matrix components in the culture conditions, as further described, for example, in Keller et al., Curr. Opin. Cell Biol. 7: 862–69, 1995, Li et al., Curr. Biol. 8: 971, 1998, Klug et al., J. Clin. Invest. 98: 216–24, 1996, Lieschke et al., Exp. Hematol. 23: 328–34, 1995, Yamane et al., Blood 90: 3516–23, 1997, and Hirashima et al., Blood 93: 1253–63, 1999.

The particular embryonic stem cell line that is used for genetic modification is not critical; exemplary murine ES cell lines include AB-1 (McMahon and Bradley, Cell 62:1073–85, 1990), E14 (Hooper et al., Nature 326: 292–95, 1987), D3 (Doetschman et al., J. Embryol. Exp. Morph. 87: 27–45, 1985), CCE (Robertson et al, Nature 323: 445–48, 1986), RW4 (Genome Systems, St. Louis, Mo.), and DBA/1lacJ (Roach et al., Exp. Cell Res. 221: 520–25, 1995).

PRODUCTION OF THE POLYPEPTIDE

According to the present invention, the production of the polypeptide of the present invention can be effected by the culturing of eukaryotic or prokaryotic expression hosts, which have been transformed with one or more polynucleotides of the present invention, in a conventional nutrient fermentation medium. The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating micro-organisms.

Thus, the present invention also provides a method for producing a polypeptide having PFI-002 activity, the method comprising the steps of (a) transforming a host cell with a nucleotide sequence shown in SEQ ID NO: 1 or a derivative, homologue, variant, analogue or fragment thereof; and (b) culturing the transformed host cell under conditions suitable for the expression of said polypeptide.

The present invention also relates to a method for producing a polypeptide having PFI-002 activity, the method comprising the steps of (a) culturing a host cell that has been transformed with a nucleotide sequence shown in SEQ ID NO: 1 or a derivative, homologue, variant, analogue or fragment thereof under conditions suitable for the expression of said polypeptide; and (b) recovering said polypeptide from the host cell culture.

The present invention also relates to a method for producing a polypeptide having PFI-002 activity, the method comprising the steps of (a) transforming a host cell with a nucleotide sequence shown in SEQ ID NO: 1 or a derivative, homologue, variant, analogue or fragment thereof; (b) culturing the transformed host cell under conditions suitable for the expression of said polypeptide; and (c) recovering said polypeptide from the host cell culture.

RIBOZYMES

Ribozymes are enzymatic RNA molecules capable of catalysing the specific cleavage of RNA. The mechanism of ribozyme action involves sequence specific hybridisation of the ribozyme molecule to complementary target RNA, followed by endonucleolytic cleavage. Within the scope of the invention are engineered hammerhead motif ribozyme molecules that specifically and efficiently catalyse endonucleolytic cleavage of PFI-002 RNA sequences.

Specific ribozyme cleavage sites within any potential RNA target are initially identified by scanning the target molecule for ribozyme cleavage sites which include the following sequences: GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridisation with complementary oligonucleotides using ribonuclease protection assays.

Both antisense RNA and DNA molecules and ribozymes of the invention may be prepared by any method known in the art for the synthesis of RNA molecules. These include techniques for chemically synthesising oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DETECTION

The presence of the PFI-002 polynucleotide coding sequence can be detected by DNA-DNA or DNA-RNA hybridisation or amplification using probes, portions or fragments of the sequence presented in SEQ ID NO: 1. Nucleic acid amplification-based assays involve the use of oligonucleotides or oligomers based on the PFI-002 coding sequence to detect transformants containing PFI-002 DNA or RNA. As used herein "oligonucleotides" or "oligomers" may refer to a nucleic acid sequence of at least about 10 nucleotides and as many as about 60 nucleotides, preferably about 15 to 30 nucleotides, and more preferably about 20 to 25 nucleotides which can be used as a probe or amplimer. Preferably, oligonucleotides are derived from the 3' region of the nucleotide sequence shown in SEQ ID NO: 1.

A variety of protocols for detecting and measuring the expression of PFI-002 polypeptide, such as by using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes on a PFI-002 polypeptide is preferred, but a competitive binding assay may also be employed. These and other assays are described, among other places, in Hampton R et al. (1990, Serological Methods, A Laboratory Manual, APS Press, St Paul, Minn., USA) and Maddox D E et al. (1983, J Exp Med 15 8:1211).

A wide variety of labels and conjugation techniques are known by those skilled in the art and can be used in various nucleic and amino acid assays. Means for producing labelled hybridisation or PCR probes for detecting PFI-002 polynucleotide sequences include oligolabelling, nick translation, end-labelling or PCR amplification using a labelled nucleotide. Alternatively, the PFI-002 coding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides.

A number of companies such as Pharmacia Biotech (Piscataway, N.J., USA), Promega (Madison, Wis., USA), and US Biochemical Corporation (Cleveland, Ohio, USA) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241. Also, recombinant immunoglobulins may be produced as shown in U.S. Pat. No. 4,816,567.

Additional methods to quantify the expression of a particular molecule include radiolabelling (Melby P C et al., 1993, J. Immunol Methods Vol 159 p235–44) or biotinylating (Duplaa C et al., 1993, Anal Biochem Vol 229 p36) nucleotides, co-amplification of a control nucleic acid, and standard curves onto which the experimental results are interpolated. Quantification of multiple samples may be speeded up by running the assay in an ELISA format where the oligomer of interest is presented in various dilutions and a spectrophotometric or calorimetric response gives rapid quantification.

Although the presence/absence of marker gene expression suggests that the gene of interest is also present, its presence and expression should be confirmed. For example, if the PFI-002 coding sequence is inserted within a marker gene sequence, recombinant cells containing PFI-002 coding regions can be identified by the absence of marker gene function. Alternatively, a marker gene can be placed in tandem with a PFI-002 coding sequence under the control of a single promoter. Expression of the marker gene in response to induction or selection usually indicates expression of PFI-002 as well.

Alternatively, host cells which contain the coding sequence for PFI-002 and express PFI-002 coding regions may be identified by a variety of procedures known to those of skill in the art. These procedures include, but are not limited to, DNA-DNA or DNA-RNA hybridisation and protein bioassay or immunoassay techniques which include membrane-based, solution-based, or chip-based technologies for the detection and/or quantification of the nucleic acid or protein.

ANTIBODIES

The amino acid sequence of the present invention can also be used to generate antibodies—such as by use of standard techniques—against the amino acid sequence.

Procedures well known in the art may be used for the production of antibodies to PFI-002 polypeptides. Such antibodies include, but are not limited to, polyclonal, monoclonal, chimeric, single chain, Fab fragments and fragments produced by a Fab expression library. Neutralising antibodies, i.e. those which antagonise biological activity of PFI-002 polypeptides, are especially preferred for diagnostics and therapeutics.

For the production of antibodies, various hosts including goats, rabbits, rats, mice, etc. may be immunised by injection with the PFI-002 polypeptide or any portion, variant, homologue, fragment, analogue or derivative thereof or oligopeptide which retains immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacili Calmette-Guerin*) and *Corynebacterium parvum* are potentially useful human adjuvants which may be employed.

Monoclonal antibodies to the amino acid sequence may be prepared using any technique which provides for the production of antibody molecules by continuous cell lines in culture. These include, but are not limited to, the hybridoma technique originally described by Koehler and Milstein (1975, Nature Vol 256 p495–497), the human B-cell hybridoma technique (Kosbor et al. (1983) Immunol Today Vol 4 p72; Cote et al. (1983) Proceedings of the National Academy of Sciences (USA) Vol 80 p2026–2030) and the EBV-hybridoma technique (Cole et al. (1985) Monoclonal Antibodies and Cancer Therapy, Alan R Liss Inc, pp. 77–96). In addition, techniques developed for the production of "chimeric antibodies", the splicing of mouse antibody genes to human antibody genes to obtain a molecule with appropriate antigen specificity and biological activity can be used (Morrison et al. (1984) Proceedings of the National Academy of Sciences (USA) Vol 81 p6851–6855; Neuberger et al. (1984) Nature Vol 312 p604–608; Takeda et al. (1985) Nature Vol 314 p452–454). Alternatively, techniques described for the production of single chain antibodies (U.S. Pat. No. 4,946,779) can be adapted to produce polypeptide-specific single chain antibodies.

Antibodies may also be produced by inducing in vivo production in the lymphocyte population or by screening recombinant immunoglobulin libraries or panels of highly specific binding reagents as disclosed in Orlandi et al. (1989, Proceedings of the National Academy of Sciences (USA) Vol 86 p 3833–3837), and Winter G and Milstein C (1991; Nature Vol 349 p293–299).

Antibody fragments which contain specific binding sites for PFI-002 may also be generated. For example, such fragments include, but are not limited to, the $F(ab')_2$ fragments which can be produced by pepsin digestion of the antibody molecule and the Fab fragments which can be generated by reducing the disulphide bridges of the $F(ab')_2$ fragments. Alternatively, Fab expression libraries may be constructed to allow rapid and easy identification of monoclonal Fab fragments with the desired specificity (Huse W D et al. (1989) Science Vol 256 p1275–1281).

An alternative technique involves screening phage display libraries where, for example the phage express scFv fragments on the surface of their coat with a large variety of complementarity determining regions (CDRs). This technique is well known in the art.

PFI-002-specific antibodies are useful for the diagnosis of conditions and diseases associated with expression of the PFI-002 receptor. A variety of protocols for competitive binding or immunoradiometric assays using either polyclonal or monoclonal antibodies with established specificities are well known in the art. Such immunoassays typically involve the formation of complexes between PFI-002 polypeptide and its specific antibody (or similar PFI-002-binding molecule) and the measurement of complex formation. A two-site, monoclonal based immunoassay utilising monoclonal antibodies reactive to two, non-interfering epitopes on a specific PFI-002 protein is preferred, but a competitive binding assay may also be employed. These assays are described in Maddox D E et al. (1983, Journal of Experimental Medicine Vol 158 p1211).

Anti-PFI-002 antibodies are useful for the diagnosis of disorders involving abnormal signal transduction or other disorders or diseases characterised by abnormal expression of a PFI-002 receptor. Diagnostic assays for PFI-002 include methods utilising the antibody and a label to detect a PFI-002 polypeptide in human body fluids, cells, tissues or sections or extracts of such tissues. The polypeptides and antibodies of the present invention may be used with or without modification. Frequently, the polypeptides and antibodies will be labelled by joining them, either covalently or noncovalently, with a reporter molecule. A wide variety of reporter molecules are known to those of skill in the art.

Antibodies may be used in method of detecting polypeptides of the invention present in biological samples by a method which comprises: (a) providing an antibody of the invention; (b) incubating a biological sample with said antibody under conditions which allow for the formation of an antibody-antigen complex; and (c) determining whether antibody-antigen complex comprising said antibody is formed.

Antibodies of the invention may be bound to a solid support and/or packaged into kits in a suitable container along with suitable reagents, controls, instructions and the like.

ASSAYS/IDENTIFICATION METHODS

The present invention also relates to an assay method for detecting the presence of PFI-002 in cells (such as human cells) comprising: (a) performing a reverse transcriptase-polymerase chain reaction (RT-PCR) on RNA (such as total RNA) from such cells using a pair of PCR primers that are specific for PFI-002, as determined from the DNA sequence shown in SEQ ID NO: 1 or an allelic variation thereof; and (b) assaying the appearance of an appropriately sized PCR fragment—such as by agarose gel electrophoresis.

There are numerous assays in which the polypeptide of the present invention can used to screen for modulators (e.g. antagonists or agonists) of the polypeptide. Examples of such assays include:

Functional Assay—One example of a method for screening receptors to identify antagonists thereof is to monitor the inhibitory or stimulatory effect on cAMP or adenylate cyclase accumulation. Such an assay involves transfecting a mammalian cell with the receptor of the present invention for cell surface expression. The cell is then exposed to putative antagonists and the amount of cAMP accumulation is measured. If the putative antagonist binds the receptor the levels of receptor-mediated cAMP or adenylate cyclase activity will either increase or decrease.

Functional Assay using a Fluorometric Imaging Plate Reader (FlipR)—A technique used for screening and includes the use of cells that express the receptor of the present invention (for example, transfected HEK293 cells) in a system that measures intracellular calcium or extracellular pH changes caused by receptor activation. In this technique, cells expressing the receptor of the invention may be contacted with compounds (e.g. small molecules, peptides, lipids, nucleotides or glycoproteins) that cause a second messenger response, e.g. signal transduction, change in calcium levels or pH changes. These changes are used to determine whether the potential compound activates or inhibits the receptor.

Ligand Binding Assay—This type of assay may test binding of a candidate compound, where adherence to the cells containing the receptor of the present invention is detected by means of a label directly or indirectly associated with the candidate compound or in an assay involving competition with a labelled competitor. Standard assays for conducting screens that determine if the compound activates or inhibits the receptor are well understood by those skilled in the art.

The present invention therefore also relates to a method of identifying agents (such as compounds, other substances or compositions comprising the same) that affect (such as antagonise, agonise or otherwise modify) the activity of PFI-002 and/or the expression thereof, the method comprising contacting PFI-002 or the nucleotide sequence coding for the same with the agent and then measuring the activity of PFI-002 and/or the expression thereof.

The present invention also relates to a method of identifying agents (such as compounds, other substances or compositions comprising the same) that selectively affect (such as antagonise, agonise or otherwise modify) the activity of PFI-002 and/or the expression thereof, the method comprising contacting PFI-002 or the nucleotide sequence coding for the same with the agent and then measuring the activity of PFI-002 and/or the expression thereof.

The present invention also relates to a method of identifying agents (such as compounds, other substances or compositions comprising the same) that affect (such as antagonise, agonise or otherwise modify) the activity of PFI-002 and/or the expression thereof, the method comprising measuring the activity of PFI-002 and/or the expression thereof in the presence of the agent or after the addition of the agent in: (a) a cell line into which has been incorporated recombinant DNA comprising the DNA sequence shown in SEQ ID NO: 1 or an allelic variation thereof, or (b) a cell population or cell line that naturally selectively expresses PFI-002. Preferably, the activity of PFI-002 is determined by the assay methods described above.

The present invention also relates to a method of identifying agents (such as compounds, other substances or compositions comprising the same) that selectively affect (such as antagonise, agonise or otherwise modify) the activity of PFI-002 and/or the expression thereof, the method comprising measuring the activity of PFI-002 and/or the expression thereof in the presence of the agent or after the addition of the agent in: (a) a cell line into which has been incorporated recombinant DNA comprising the DNA sequence shown in SEQ ID NO: 1 or an allelic variation thereof, or (b) a cell population or cell line that naturally selectively expresses PFI-002. Preferably, the activity of PFI-002 is determined by the assay methods described above.

The present invention also relates to a method of screening an agent for modulation (preferably for specific modulation) of PFI-002 (or a derivative, homologue, variant, analogue or fragment thereof) activity or the expression of the nucleotide sequence coding for the same (including a derivative, homologue, variant, analogue or fragment thereof), the method comprising the steps of: (a) providing a candidate agent; (b) combining PFI-002 (or the derivative, homologue, variant, analogue or fragment thereof) or the nucleotide sequence coding for the same (or the derivative, homologue, variant, analogue or fragment thereof) with the candidate agent for a time sufficient to allow modulation under suitable conditions; and (c) detecting modulation of the candidate agent to PFI-002 (or the derivative, homologue, variant, analogue or fragment thereof) or the nucleotide sequence coding for the same (or the derivative, homologue, variant, analogue or fragment thereof) in order to ascertain if the candidate agent modulates PFI-002 (or the derivative, homologue, variant, analogue or fragment thereof) activity or the expression of the nucleotide sequence coding for the same (or the derivative, homologue, variant, analogue or fragment thereof).

The present invention also relates to a method of screening an agent for specific binding affinity with PFI-002 (or a derivative, homologue, variant, analogue or fragment thereof) or the nucleotide sequence coding for the same (including a derivative, homologue, variant, analogue or fragment thereof), the method comprising the steps of: (a) providing a candidate agent; (b) combining PFI-002 (or the derivative, homologue, variant, analogue or fragment thereof) or the nucleotide sequence coding for the same (or the derivative, homologue, variant, analogue or fragment thereof) with the candidate agent for a time sufficient to allow binding under suitable conditions; and (c) detecting binding of the candidate agent to PFI-002 (or the derivative, homologue, variant, analogue or fragment thereof) or the nucleotide sequence coding for the same (or the derivative, homologue, variant, analogue or fragment thereof).

Thus, in certain embodiments of the present invention, PFI-002 or a variant, homologue, fragment, analogue or derivative thereof and/or a cell line that expresses the PFI-002 or variant, homologue, fragment, analogue or derivative thereof may be used to screen for antibodies, peptides, or other agents, such as organic or inorganic molecules, that act as modulators (e.g. antagonists or agonists) of PFI-002 activity or for the expression thereof, thereby identifying a therapeutic agent capable of modulating the receptor. Alternatively, screening of peptide libraries or organic libraries made by combinatorial chemistry with recombinantly expressed PFI-002 or a variant, homologue, fragment, analogue or derivative thereof or cell lines expressing PFI-002 or a variant, homologue, fragment, analogue or derivative thereof may be useful for identification of therapeutic agents that function by modulating the receptor. Synthetic compounds, natural products, and other sources of potentially biologically active materials can be screened in a number of ways deemed to be routine to those of skill in the art. For example, nucleotide sequences encoding the N-terminal region of PFI-002 may be expressed in a cell line, which can be used for screening of allosteric modulators, either agonists or antagonists, of PFI-002 activity.

A PFI-002 polypeptide, its immunogenic fragments or oligopeptides thereof can be used for screening therapeutic compounds in any of a variety of drug screening techniques. The polypeptide employed in such a test may be free in solution, affixed to a solid support, borne on a cell surface, or located intracellularly. The formation of binding complexes between a PFI-002 polypeptide and the agent being tested may be measured.

Accordingly, the present invention relates to a method for screening one or a plurality of compounds for modulation (preferably specific modulation, such as specific binding affinity) of PFI-002 or the expression thereof, or a portion thereof or variant, homologue, fragment, analogue or derivative thereof, comprising providing one or a plurality of compounds; combining a PFI-002 or a nucleotide sequence coding for the same or a portion thereof or variant, homologue, fragment, analogue or derivative thereof with the or each of a plurality of compounds for a time sufficient to allow modulation under suitable conditions; and detecting binding of a PFI-002, or portion thereof or variant, homologue, fragment, analogue or derivative thereof, to each of the plurality of compounds, thereby identifying the compound or compounds which modulate a PFI-002 or a nucleotide sequence coding for the same. In such an assay, the plurality of compounds may be produced by combinatorial chemistry techniques known to those of skill in the art.

Another technique for drug screening provides for high throughput screening (HTS) of compounds having suitable binding affinity to the PFI-002 polypeptides and is based upon the method described in detail in Geysen, WO 84/03564, published on Sep. 13, 1984. In summary, large numbers of different small peptide test compounds are synthesized on a solid substrate, such as plastic pins or some other surface. The peptide test compounds are reacted with PFI-002 fragments and washed. A bound PFI-002 is then detected—such as by appropriately adapting methods well known in the art. A purified PFI-002 can also be coated directly onto plates for use in the aforementioned drug screening techniques. Alternatively, non-neutralising antibodies can be used to capture the peptide and immobilise it on a solid support.

This invention also contemplates the use of competitive drug screening assays in which neutralising antibodies capable of binding a PFI-002 polypeptide specifically compete with a test compound for binding a PFI-002. In this manner, the antibodies can be used to detect the presence of any peptide which shares one or more antigenic determinants with a PFI-002.

The assay method of the present invention may be a high throughput screen (HTS). In this regard, the teachings of WO 84/03564 may be adapted for the PFI-002 of the present invention.

The teachings of U.S. Pat. No. 5,738,985 may also be adapted for the assay method of the present invention.

AGENTS

The present invention also provides one or more agents identified by the assays methods and identification methods of the present invention.

The agent of the present invention can be, for example, an organic compound or an inorganic compound. The agent can be, for example, a nucleotide sequence that is antisense to all or part of the sequence shown in SEQ ID NO: 1.

The invention further provides an agent of the present invention (or even a pharmaceutically acceptable salt thereof, or a pharmaceutically acceptable solvate thereof) or a pharmaceutical composition containing any of the foregoing, for use as a medicament.

The present invention also relates to the use of an agent to affect PFI-002 activity (such as to antagonise, modulate or agonise its GPCR activity).

DIAGNOSTICS

The present invention also provides a diagnostic composition for the detection of PFI-002 polynucleotide sequences. The diagnostic composition may comprise the sequence shown in SEQ ID NO: 1 or a variant, homologue, fragment, analogue or derivative thereof, or a sequence capable of hybridising to all or part of the nucleotide sequence shown in SEQ ID NO: 1 or an allelic variation thereof.

In order to provide a basis for the diagnosis of disease, normal or standard values from a PFI-002 polypeptide expression should be established. This is accomplished by combining body fluids or cell extracts taken from normal subjects, either animal or human, with antibody to a PFI-002 polypeptide under conditions suitable for complex formation which are well known in the art. The amount of standard complex formation may be quantified by comparing it to a dilution series of positive controls where a known amount of antibody is combined with known concentrations of a purified PFI-002 polypeptide. Then, standard values obtained from normal samples may be compared with values obtained from samples from subjects potentially affected by a disorder or disease related to a PFI-002 polypeptide expression. Deviation between standard and subject values establishes the presence of the disease state.

A PFI-02 polynucleotide, or any part thereof, may provide the basis for a diagnostic and/or a therapeutic compound. For diagnostic purposes, PFI-002 polynucleotide sequences may be used to detect and quantify gene expression in conditions, disorders or diseases in which PFI-002 activity may be implicated.

PFI-002-encoding polynucleotide sequence may be used for the diagnosis of diseases resulting from expression of PFI-002. For example, polynucleotide sequences encoding PFI-002 may be used in hybridisation or PCR assays of tissues from biopsies or autopsies or biological fluids, such as serum, synovial fluid or tumour biopsy, to detect abnormalities in PFI-002 expression. The form of such qualitative or quantitative methods may include Southern or northern analysis, dot blot or other membrane-based technologies; PCR technologies; dip stick, pin or chip technologies; and ELISA or other multiple sample format technologies. All of these techniques are well known in the art and are, in fact, the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for PFI-002 expression should be established. This is accomplished by combining body fluids or cell extracts taken from normal subjects, either animal or human, with PFI-002 or a portion thereof, under conditions suitable for hybridisation or amplification. Standard hybridisation may be quantified by comparing the values obtained for normal subjects with a dilution series of positive controls run in the same experiment where a known amount of purified PFI-002 is used. Standard values obtained from normal samples may be compared with values obtained from samples from subjects potentially affected by a disorder or disease related to expression of the PFI-002 coding sequence. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

Thus, the present invention relates to the use of a PFI-002 polypeptide, or variant, homologue, fragment, analogue or derivative thereof, to produce anti-PFI-002 antibodies which can, for example, be used diagnostically to detect and quantify PFI-002 levels in disease states.

The present invention further relates to diagnostic assays and kits for the detection of PFI-002 in cells and tissues comprising a purified PFI-002 which may be used as a positive control, and anti-PFI-002 antibodies. Such antibodies may be used in solution-based, membrane-based, or tissue-based technologies to detect any disease state or condition related to the expression of PFI-002 protein or expression of deletions or a variant, homologue, fragment, analogue or derivative thereof.

PROBES

Another aspect of the subject invention is the provision of nucleic acid hybridisation or PCR probes which are capable of detecting polynucleotide sequences, including genomic sequences, encoding PFI-002 coding region or closely related molecules, such as alleles. The specificity of the probe, i.e. whether it is derived from a highly conserved, conserved or non-conserved region or domain, and the stringency of the hybridisation or amplification (high, intermediate or low) will determine whether the probe identifies only naturally occurring PFI-002 coding sequence, or related sequences. Probes for the detection of related nucleic acid sequences are selected from conserved or highly conserved nucleotide regions of PFI-002 polynucleotides, such as the 3' region, and such probes may be used in a pool of degenerate probes. For the detection of identical nucleic acid sequences, or where maximum specificity is desired, nucleic acid probes are selected from the non-conserved nucleotide regions or unique regions of PFI-002 polynucleotides. As used herein, the term "non-conserved nucleotide region" refers to a nucleotide region that is unique to the PFI-002 coding sequence disclosed herein and does not occur in related sequences. PCR, as described in U.S. Pat. No. 4,683,195, U.S. Pat. No. 4,800,195 and U.S. Pat. No. 4,965,188 provides additional uses for oligonucleotides based upon the PFI-002 sequence. Such oligomers are generally chemically synthesized, but they may be generated enzymatically or produced from are combinant source. Oligomers generally comprise two nucleotide sequences, one with sense orientation (5'→3') and one with antisense (3'←5') employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

The nucleic acid sequence for PFI-002 can also be used to generate hybridisation probes as previously described, for mapping the endogenous genomic sequence. The sequence may be mapped to a particular chromosome or to a specific region of the chromosome using well known techniques. These include in situ hybridisation to chromosomal spreads, (Verma et al. (1988) Human Chromosomes: A Manual of Basic Techniques, Pergamon Press, New York City, USA), flow-sorted chromosomal preparations, or artificial chromosome constructions such as yeast artificial chromosomes (YACs), bacterial artificial chromosomes (BACs), bacterial PI constructions or single chromosome cDNA libraries.

In situ hybridisation of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localised by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal, carrier or affected individuals.

PHARMACEUTICALS

The present invention also provides a pharmaceutical composition for treating an individual in need of the same due to PFI-002 activity, the composition comprising a therapeutically effective amount of an agent that modulates (such as antagonises or agonises) said activity and a pharmaceutically acceptable carrier, diluent, excipient or adjuvant.

Thus, the present invention also covers pharmaceutical compositions comprising the agents of the present invention (an agent capable of modulating the expression pattern of the nucleotide sequence of the present invention or the activity of the expression product thereof and/or an agent identified by an assay according to the present invention). In this regard, and in particular for human therapy, even though the agents of the present invention can be administered alone, they will generally be administered in admixture with a pharmaceutical carrier, adjuvant, excipient or diluent selected with regard to the intended route of administration and standard pharmaceutical practice.

By way of example, in the pharmaceutical compositions of the present invention, the agents of the present invention may be admixed with any suitable binder(s), lubricant(s), suspending agent(s), coating agent(s), or solubilising agent(s).

In general, a therapeutically effective daily oral or intravenous dose of the agents of the present invention is likely to range from 0.01 to 50 mg/kg body weight of the subject to be treated, preferably 0.1 to 20 mg/kg. The agents of the present invention may also be administered by intravenous infusion, at a dose which is likely to range from 0.001–10 mg/kg/hr.

Thus, the present invention also provides a method of treating an individual in need of the same due to PFI-002 activity comprising administering to said individual an effective amount of the pharmaceutical composition of the present invention.

Typically, the physician will determine the actual dosage which will be most suitable for an individual patient and it will vary with the age, weight, sex and response of the particular patient. The above dosages are exemplary of the average case. There can, of course, be individual instances where higher or lower dosage ranges are merited, and such are within the scope of this invention.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For oral, parenteral, buccal and sublingual administration to subjects (such as patients), the daily dosage level of the agents of the present invention may typically be from 10 to 500 mg (in single or divided doses). Thus, and by way of example, tablets or capsules may contain from 5 to 100 mg of active agent for administration singly, or two or more at a time, as appropriate. It is also possible to administer the agents of the present invention in sustained release formulations.

In some applications, generally in humans, oral administration of the agents of the present invention is the preferred route, being the most convenient and can in some cases avoid disadvantages associated with other routes of administration—such as those associated with intracavernosal (i.c.) administration. In circumstances where the recipient suffers from a swallowing disorder or from impairment of drug absorption after oral administration, the drug may be administered parenterally, sublingually or buccally.

For veterinary use, the agent of the present invention is typically administered as a suitably acceptable formulation in accordance with normal veterinary practice and the veterinary surgeon will determine the dosing regimen and route of administration which will be most appropriate for a particular animal. However, as with human treatments, it may be possible to administer the agent alone for veterinary treatments.

Typically, the pharmaceutical compositions—which may be for human or animal usage—will comprise any one or more of a pharmaceutically acceptable diluent, carrier, excipient or adjuvant. The choice of pharmaceutical carrier, excipient, adjuvant or diluent can be selected with regard to the intended route of administration and standard pharmaceutical practice. As indicated above, the pharmaceutical compositions may comprise as—or in addition to—the carrier, excipient, adjuvant or diluent any suitable binder(s), lubricant(s), suspending agent(s), coating agent(s) or solubilising agent(s).

In some embodiments of the present invention, the pharmaceutical compositions will comprise one or more of: an agent that has been screened by an assay of the present invention; an agent that is capable of interacting with SEQ ID NO: 1 or SEQ ID NO: 2 including derivatives, fragments, homologues, analogues or variants thereof or sequences capable of hybridising to the nucleotide sequence shown in SEQ ID NO: 1.

Included in the scope of the invention are oligonucleotide sequences, antisense RNA and DNA molecules and ribozymes, which function to destabilise PFI-002 mRNA or inhibit translation of PFI-002.

A PFI-002 antisense molecule may provide the basis for treatment of various abnormal conditions related to, for example, increased PFI-002 activity.

Expression vectors derived from retroviruses, adenovirus, herpes or vaccinia viruses, or from various bacterial plasmids, may be used for delivery of recombinant PFI-002 sense or antisense molecules to the targeted cell population. Methods which are well known to those skilled in the art can be used to construct recombinant vectors containing PFI-002. Alternatively, recombinant PFI-002 can be delivered to target cells in liposomes.

The full length cDNA sequence and/or its regulatory elements enable researchers to use PFI-002 as a tool in sense (Youssoufian H and H F Lodish (1993) Mol Cell Biol 13:98–104) or antisense (Eguchi et al (1991) Annu Rev Biochem 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions. Appropriate oligonucleotides, which can be 20 nucleotides in length, may be used to isolate PFI-002 sequences or closely related molecules from human libraries.

Additionally, PFI-002 expression can be modulated by transfecting a cell or tissue with expression vectors which express high levels of a PFI-002 fragment in conditions where it would be preferable to block PFI-002 activity. Such constructs can flood cells with untranslatable sense or anti-sense sequences. Even in the absence of integration into the DNA, such vectors may continue to transcribe RNA molecules until all copies of the vector are disabled by endogenous nucleases. Such transient expression may last for a month or more with a non-replicating vector and even longer if appropriate replication elements are part of the vector system.

Modifications of gene expression can be obtained by designing antisense sequences to the control regions of the PFI-002 gene, such as the promoters, enhancers, and introns.

Oligonucleotides derived from the transcription initiation site, e.g. between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base-pairing. Triple helix pairing compromises the ability of the double helix to open sufficiently for the binding of polymerases, transcription factors, or regulatory molecules.

Thus the invention provides a pharmaceutical composition comprising an agent of the present invention (or even a pharmaceutically acceptable salt thereof, or a pharmaceutically acceptable solvate thereof) together with a pharmaceutically acceptable diluent, adjuvant, excipient or carrier.

The pharmaceutical composition could be for veterinary (i.e. animal) usage or for human usage.

Thus, the present invention therefore also relates to pharmaceutical compositions comprising effective amounts of modulators (e.g. antagonists or agonists) of PFI-002 protein (including antisense nucleic acid sequences) in admixture with a pharmaceutically acceptable diluent, carrier, excipient or adjuvant (including combinations thereof).

The present invention relates to pharmaceutical compositions which may comprise all or portions of PFI-002 polynucleotide sequences, PFI-002 antisense molecules, PFI-002 polypeptides, protein, peptide or organic modulators of PFI-002 bioactivity, such as antagonists (including antibodies) or agonists, alone or in combination with at least one other agent, such as stabilising compound, and may be administered in any sterile, biocompatible pharmaceutical carrier, including, but not limited to, saline, buffered saline, dextrose, and water.

GENERAL METHODOLOGY REFERENCES

Although in general the techniques mentioned herein are well known in the art, reference may be made in particular to Sambrook et al., Molecular Cloning, A Laboratory Manual (1989) and Ausubel et al., Short Protocols in Molecular Biology (1999) $4^{th}$ Ed, John Wiley & Sons, Inc. PCR is described in U.S. Pat. No. 4,683,195, U.S. Pat. No. 4,800,195 and U.S. Pat. No. 4,965,188.

DEPOSITS

The following sample was deposited in accordance with the Budapest Treaty at the recognised depositary The National Collections of Industrial and Marine Bacteria Limited (NCIMB) at 23 St. Machar Drive, Aberdeen, Scotland, AB2 1RY, United Kingdom on 23 Aug. 2000:

NCIMB number NCIMB 41066 is *Escherichia coli* Pfi-002.

The depositor was Pfizer Central Research, Pfizer Limited, Ramsgate Road, Sandwich, Kent, CT13 9NJ, United Kingdom.

One skilled in the art could readily grow the above-mentioned *E. coli* clone (NCIMB 41066) in Luria Broth containing ampicillin and isolate the plasmid DNA of the clone using the alkali lysis method as described in Sambrook, et al., eds. (1989) Molecular Cloning: A Laboratory Manual, Cold Spring Harbor Laboratory Press, New York, N.Y., USA. The di-deoxy termination method as described by Sanger et al. (Proceedings of the National Academy of Sciences (USA) (December 1977), 74(12) :5463–5467) and modified by Applied Biosystems (see Applied Biosystems manufacturer's literature) for fluorescent detection could then be used to sequence the DNA and identify PFI-002.

The present invention also encompasses sequences derivable and/or expressable from that deposit and embodiments comprising the same. The present invention also encompasses partial sequences derivable and/or expressable from that deposit and embodiments comprising the same, wherein those partial sequences code for active polypeptides. The present invention also encompasses proteins comprising sequences derivable and/or expressable from that deposit and embodiments comprising the same. The present invention also encompasses proteins comprising partial sequences derivable and/or expressable from that deposit and embodiments comprising the same, wherein those partial sequences code for active polypeptides.

INTRODUCTION TO THE EXAMPLES SECTION, THE FIGURES AND THE SEQUENCE LISTING

The present invention will now be described, by way of example only, with reference to the accompanying Figures and Sequence Listing in which:

FIG. 1 shows a schema for the bioinformatic analysis of PFI-002 (db=database).

Figure 2:
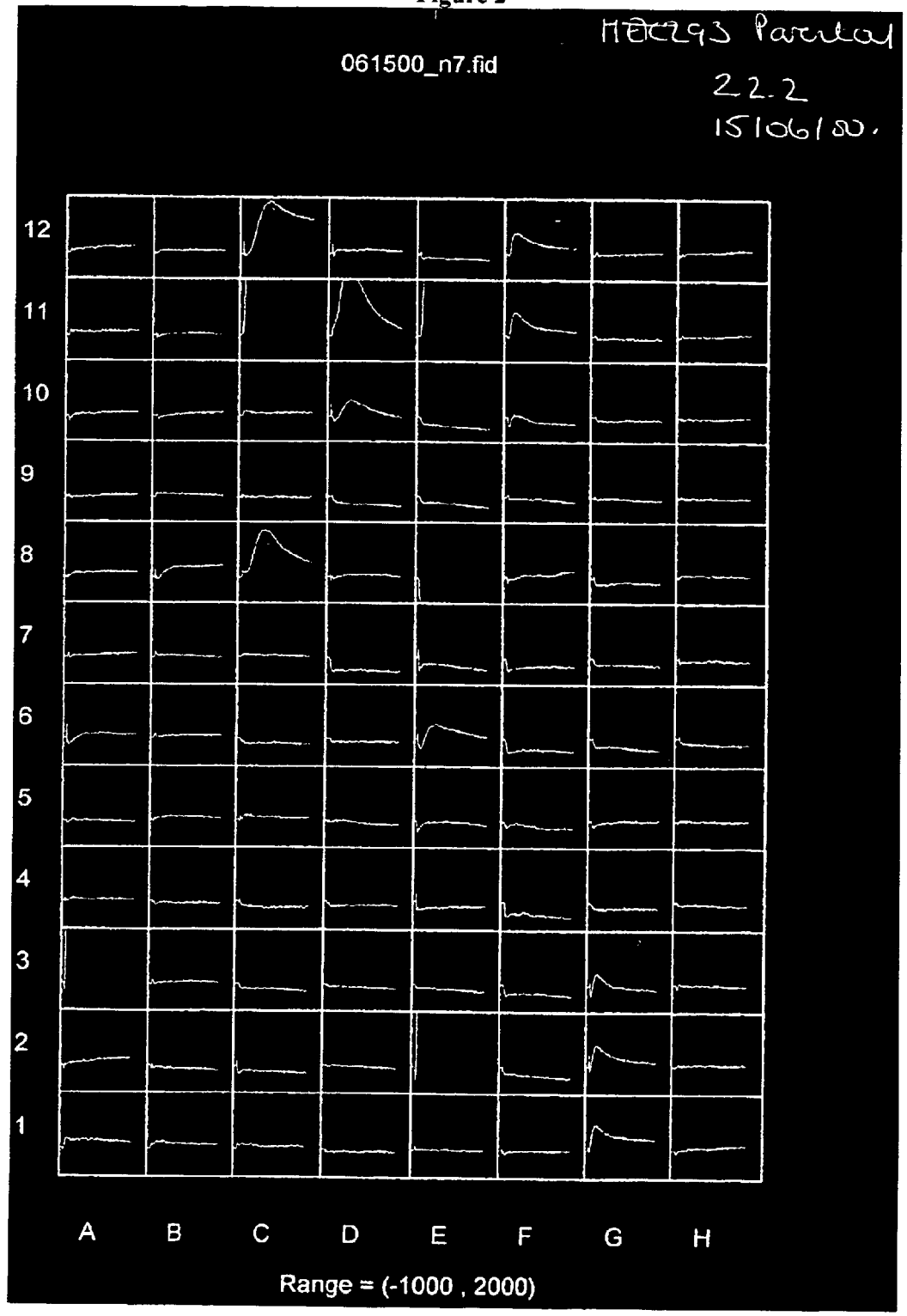
FIG. 2 shows the specific functional response of PFI-002 receptor to neuromedin U. The grid corresponds to a 96 well plate and each square of the grid corresponds to one screened peptide (see list of screened peptides under FUNCTIONAL STUDIES section below—e.g. square A1 relates to the result for peptide Arg-Gly-Asp-Ser (RGDS); square B1 relates to the result for peptide [Arg8]Vasopressin, etc.).

FIG. 2 shows the specific functional response of PFI-002 receptor to neuromedin U. The grid corresponds to a 96 well plate and each square of the grid corresponds to one screened peptide (see list of screened peptides under FUNCTIONAL STUDIES section below—e.g. square A1 relates to the result for peptide Arg-Gly-Asp-Ser (RGDS); square B1 relates to the result for peptide [Arg8]Vasopressin, etc.).

FIG. 3 shows a ClustalW alignment of PFI-002 with SW|P20789|NTR1__RAT NEUROTENSIN RECEPTOR TYPE 1 (NT-R-1).

FIG. 4 shows a ClustalW alignment of PFI-002 with GB|AF044601|NMUR1__Human NEUROMEDIN RECEPTOR TYPE 1 (NMU-R-1).

FIG. 5A shows SEQ ID NO: 1 which is the nucleotide sequence coding for PFI-002. The ATG translation initiation codon is indicated by the first three letters. The stop codon is indicated by the last three letters.

FIG. 5B shows SEQ ID NO: 2 shows the corresponding amino acid sequence coding for PFI-002.

FIG. 6 shows SEQ ID NOS: 3–6 which are the various primers used throughout the Examples.

The polynucleotide which encodes the GPCR of the present invention was cloned and the DNA and amino acid sequences analysed using various bioinformatic tools. The GPCR encoded by the sequences described herein has been termed PFI-002.

EXAMPLES

IDENTIFICATION OF PFI-002

PFI-002 was identified in unannotated genomic sequence from chromosome 5.(GenBank contig AC008571) which was released by the Genome Sequencing Centers by searching the sequences with known members of the G-protein coupled receptor (GPCR) family using the BLAST algorithm.

PFI-002 sequence was found amongst the following public and Incyte (USA) expressed sequence tags (ESTs):

| Public ESTs | | | |
|---|---|---|---|
| g1186640 | Nervous System | yy59b04 | multiple sclerosis |
| g766966 | Nervous System | yf62a02 | brain, infant |
| g876179 | Nervous System | ym13d04 | brain, infant |
| Incyte ESTs | | | |
| 621183H1 | Endocrine System | 621183 | paraganglion tumor |

This suggests that the PFI-002 gene is expressed in the nervous system and possibly tumour cells.

BIOINFORMATIC STUDIES

In order to confirm that PFI-002 was a member of the GPCR family, a number of bioinformatics approaches were performed.

(a) BLAST Search Against Swissprot

PFI-002 was searched against Swissprot using the BLAST algorithm (Basic Local Alignment Search Tool (Altshul S F (1993) J. Mol. Evol. 36:290–300; Altshul, S F et al (1990) J. Mol. Biol. 215:403–410)) to identify the closest protein match. In this case the top hit was to:

SW|P20789|NTR1__RAT NEUROTENSIN RECEPTOR TYPE 1 (NT-R-1) (HIGH-A . . . )

These results indicate that PFI-002 is a member of the GPCR family.

(b) ClustalW Alignment of PFI-002 with SW|P20789|NTR1__RAT NEUROTENSIN RECEPTOR TYPE 1 (NT-R-1)

These results are shown in FIG. 3.

(c) BLAST Search Against a Non-redundant Human GPCR Database

PFI-002 was searched against a non-redundant human GPCR database comprising, mainly sequences from Genbank and Geneseq Patents databases in order to identify the class of agonist for this receptor. The top ten hits are shown below:

| | |
|---|---|
| AF044601 NMUR1 | e-value = 5e-73, % Identity = 56% |
| AF034632 MOTILIN | e-value = 1e-31, % Identity = 37% |
| P30989 NTR1 | e-value = 2e-30, % Identity = 35% |
| U60179 GHSR | e-value = 3e-25, % Identity = 32% |
| Y10148 NTR2 | e-value = 4e-24, % Identity = 31% |
| P16473 TRFR | e-value = 4e-23, % Identity = 33% |
| P30874 SSR2 | e-value = 4e-22, % Identity = 31% |
| P35372 OPRM | e-value = 7e-22, % Identity = 31% |
| P30556 AT1B | e-value = 6e-21, % Identity = 31% |
| L08893 BRS3 | e-value = 8e-21, % Identity = 26%. |

(e value=statistical likelihood of the hit occurring by chance)

These results demonstrate that PFI-002 is most closely similar to neuromedin U receptors and they suggest that PFI-002 encodes a novel GPCR whose ligand is likely to be neuromedin U.

(d) ClustalW Alignment of PFI-002 with GB|AF044601|NMUR1__Human NEUROMEDIN RECEPTOR TYPE 1 (NMU-R-1)

These results are shown in FIG. 4.

ISOLATION OF PFI-002

Full-length coding sequence of PFI-002 was cloned from colon poly $A^+$ RNA, using the thermoscript reverse transcriptase-polymerase chain reaction (RT-PCR) system (Life Technologies, Inc.) according to the manufacturer's instructions.

Reverse transcription: The 3'-5' gene specific primer used in the RT reaction was:

GSP1: 5'-GCTCTGAAAGAATTCAGGTTTTG-3' (SEQ ID NO: 4)

RT reaction: 500 ng human colon poly $A^+$ RNA, 1 µl GSP1 (10 µM stock), made up to 10 µl with $H_2O$. Proceeded as detailed in the manufacturer's instructions.

PCR: 2 µl of the RT reaction was used per PCR reaction following the manufacturer's protocol.

5'-3' primer: GSP2 5'-ACCATGGCAGGGATGG-AAAAACTT-3' (SEQ ID NO: 3)

3'-5' primer: GSP1 5'-GCTCTGAAAGAATTCAGG-TTTTG-3' (SEQ ID NO: 4)

PCR conditions: 94° C.—2 minutes, then 30 cycles of 94° C.—1 minute, 58° C.—1 minute, 68° C.—2 minutes. Final cycle was 68° C.—14 minutes.

The PFI-002 PCR product was gel extracted using the QIAgen gel extraction kit, according to the manufacturer's instructions. The resultant product was TA cloned (Invitrogen TA cloning methodology) into the vector pcDNA3.1/V5-His-TOPO (Invitrogen), according to the manufacturer's instructions.

TISSUE DISTRIBUTION

Forward Primer A1: 5'-TCCAGAAACACCTG-AACAGC-3' (SEQ ID NO: 5)

Reverse Primer A2: 5'-GAGGTAGAATAGGAA-GGAGG-3' (SEQ ID NO: 6)

Expected product size=615 bp

PCR carried out on 250 ng of human tissue cDNA over 40 cycles.

PCR reaction set up as follows: dNTPs (10 mM)—1 µl, Primer A1 (10 µM)—1 µl, Primer A2 (10 µM)—1 µl, 5×reaction buffer—10 µl, Elongase (Life Technologies, Inc.)—1 µl, cDNA—250 µg, made up to 50 µl with H$_2$O.

Results

| Tissue | PFI-002 | Tissue | PFI-002 |
|---|---|---|---|
| Fetal Brain | − | Fetal heart | − |
| Cerebellum | +++ | Liver | − |
| Dorsal Root Ganglia | − | Lung | ++ |
| Bladder | − | Hela | − |
| Heart | − | Stomach | +++ |
| Kidney | ++ | Small intestine | − |
| Fetal kidney | +++ | Colon | + |
| Testis | +++ | Spleen | − |

Key to Table:
−: not detected,
+: low expression,
+++: high expression

FUNCTIONAL STUDIES

Transient Expression in Native HEK 293 Cells

Transfection: 7.5 µg of PFI-002 DNA was transiently transfected into native human embryonic kidney 293 (HEK 293) cells (75 cm$^2$ flask, 80% confluent) using the Lipofectamine Plus protocol (Life Technologies, Inc.) and following the manufacturer's instructions. 24 hrs after transfection, the cells were detached with trypsin and seeded into black walled 96 well plates at a density of 5×10$^4$ cells/well. The next day the cells were loaded with Fluo-3 in the presence of 3 mM probenicid (Molecular Devices; inhibits activity of the anion transport protein, thus improving dye loading) for 1.5 hours (loading dye/96 well plate: 50 µg Fluo-3 in 20 µl DMSO+20 µl 20% pluronic acid in DMSO+11 ml growth media+3 mM probenicid—added 100 µl loading dye/well). After washing (wash buffer PBS/3 mM probenicid/pH 7.4), the cells were exposed to 60 peptides (final concentration 5 µM each) arrayed in a 96 well plate. In addition, neuromedins B, C, N, U8 and U25 (final concentration 10 µM each) were screened in triplicate. Fluorescence was measured by a Fluorometric Imaging Plate Reader (FLIPR, Molecular Devices) according to the manufacturer's protocol.

Screened Peptides:

| Location on 96 well plate (see FIG. 2) | Peptide |
|---|---|
| A1 | Arg-Gly-Asp-Ser (RGDS) |
| A2 | Adrenocorticotrophic hormone (1-39), human (ACTH) |
| A3 | Pituitary adenylate cyclase activating peptide (1-27) |
| A4 | Neuropeptide Y, human, rat (NPY) |
| A5 | Guanylin (rat) |
| A6 | alpha-Calcitonin gene-related peptide, human (CGRP) |
| A7 | beta-Melanocyte stimulating hormone, human (beta-MSH) |
| A8 | Melanin-concentrating cormone, human, rat, mouse (MCH) |
| A9 | Somatostatin-14 |
| A10 | Inhibin beta-subunit fragment (67-94), human |
| A11 | Thyrotropin-releasing hormone (TRH) |
| A12 | Angiotensin II, human |
| B1 | [Arg8]Vasopressin |
| B2 | [Arg8]Vasotocin (AVT) |
| B3 | Substance P |
| B4 | Bradykinin |
| B5 | Neurokinin B |
| B6 | Cholecystokinin sulfated (CCK-8 sulfated) |
| B7 | Bombesin |
| B8 | Calcitonin, human |
| B9 | Oxytocin |
| B10 | Dynorphin A |
| B11 | beta-Endorphin, human |
| B12 | Leu-enkephalin |
| C1 | Met-enkephalin |
| C2 | Brain natriuretic peptide-32, porcine |
| C3 | N-Formyl-Met-Leu-Phe |
| C4 | Nociceptin (Orphanin FQ) |
| C5 | Urodilatin |
| C6 | Gastrin I, human |
| C7 | Neuromedin B |
| C8 | Urocortin, rat |
| C9 | Leptin fragment (22-56), human |
| C10 | Neurokinin A |
| C11 | Vasoactive intestinal peptide, human, bovine, porcine, rat (VIP) |
| C12 | Secretin, human |
| D1 | Brain injury-derived neurotrophic peptide (BINP) |
| D2 | Endomorphin-1 |
| D3 | Endomorphin-2 |
| D4 | Luteinizing hormone releasing hormone (LHRH) |
| D5 | Neuromedin N, porcine |
| D6 | Nocistatin, bovine |
| D7 | Motilin, porcine |
| D8 | gamma-Melanocyte stimulating hormone (gamma-MSH) |
| D9 | Neurotensin |
| D10 | Parathyroid hormone (1-34), human |
| D11 | Sauvagine, frog |
| D12 | Valosin, porcine |
| E1 | Neuropeptide FF (F-8-F-NH2) |
| E2 | Peptide histidine methionine-27, human (PHM-27) |
| E3 | Enterostatin, human |
| E4 | Gastrin-releasing peptide, human |
| E5 | beta-Amyloid peptide (1-28) |
| E6 | CRF (human, rat) |
| E7 | Galanin, human |
| E8 | Kinetensin, human, rat |
| E9 | Antiflammin-1 |
| E10 | Antiflammin-2 |
| E11 | Mastoparan, wasp |
| E12 | Peptide YY, human |
| F1 | Neuromedin B |
| F2 | Neuromedin B |
| F3 | Neuromedin B |
| F4 | Neuromedin C |
| F5 | Neuromedin C |
| F6 | Neuromedin C |
| F7 | Neuromedin N |
| F8 | Neuromedin N |
| F9 | Neuromedin N |
| F10 | Neuromedin U8 |
| F11 | Neuromedin U8 |
| F12 | Neuromedin U8 |

| Location on 96 well plate (see FIG. 2) | Peptide |
|---|---|
| G1 | Neuromedin U25 |
| G2 | Neuromedin U25 |
| G3 | Neuromedin U25 |

The results of the screen can be seen in FIG. 2, which indicates the specific functional response of PFI-002 receptor to neuromedin U. All other responses seen in FIG. 2 are the result of endogenously expressed receptors which are native to the parental cell line HEK 293.

It will be appreciated that the foregoing is provided by way of example only and modification of detail may be made without departing from the scope of the invention.

What is claimed is:

1. An isolated or purified polynucleotide comprising a polynucleotide selected from the group consisting of:
   (a) a polynucleotide encoding the polypeptide of SEQ ID NO: 2;
   (b) a polynucleotide of SEQ ID NO: 1;
   (c) a polynucleotide contained in the clone deposited as National Collections of Industrial and Marine Bacteria Limited (NCIMB) 41066; and
   (d) a polynucleotide comprising a nucleotide sequence that has at least 95% identity to the polynucleotide of any one of (a) to (c) and encodes a neuromedin U receptor that mediates, in HEK-293 cells transfected with and expressing said polynucleotide, a specific, neuromedin U-induced increase in intracellular calcium following contact with neuromedin U.

2. An expression vector comprising a polynucleotide of claim 1.

3. A cultured host cell transformed or transfected with the expression vector of claim 2.

4. A process for producing a polypeptide encoded by the polynucleotide of claim 1 comprising culturing a host cell transformed or transfected with an expression vector comprising the polynucleotide of claim 1.

5. A membrane preparation of a cell transformed or transfected with an expression vector comprising the polynucleotide of claim 1, wherein said membrane comprises a polypeptide encoded by the polynucleotide of claim 1 at an increased level as compared to a membrane preparation from a cell of the same cell type which is not transformed or transfected with an expression vector.

6. An isolated or purified polynucleotide comprising a polynucleotide sequence which encodes the polypeptide of SEQ ID NO: 2.

7. The isolated or purified polynucleotide of claim 6, wherein said polynucleotide comprises the polynucleotide of SEQ ID NO: 1.

8. An isolated or purified polynucleotide comprising the DNA contained in the NCIMB deposit 41066.

* * * * *